(12) United States Patent
Shipp et al.

(10) Patent No.: US 10,844,126 B2
(45) Date of Patent: Nov. 24, 2020

(54) ANTI-GALECTIN-1 (GAL1) MONOCLONAL ANTIBODIES AND FRAGMENTS THEREOF FOR NEUTRALIZING GAL1

(71) Applicant: Dana-Farber Cancer Institute, Inc., Boston, MA (US)

(72) Inventors: Margaret A. Shipp, Wellesley, MA (US); Jing Ouyang, Sharon, MA (US); Scott J. Rodig, Westwood, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 16/050,513

(22) Filed: Jul. 31, 2018

(65) Prior Publication Data

US 2019/0127473 A1   May 2, 2019

Related U.S. Application Data

(62) Division of application No. 14/907,418, filed as application No. PCT/US2014/047784 on Jul. 23, 2014, now abandoned.

(60) Provisional application No. 61/857,839, filed on Jul. 24, 2013, provisional application No. 61/911,031, filed on Dec. 3, 2013.

(51) Int. Cl.
| | |
|---|---|
| *A61K 39/00* | (2006.01) |
| *C07K 5/00* | (2006.01) |
| *C12N 5/20* | (2006.01) |
| *G01N 33/53* | (2006.01) |
| *C07K 16/28* | (2006.01) |
| *G01N 33/574* | (2006.01) |
| *C07K 16/18* | (2006.01) |
| *G01N 33/577* | (2006.01) |
| *G01N 33/68* | (2006.01) |

(52) U.S. Cl.
CPC ...... *C07K 16/2851* (2013.01); *A61K 39/0005* (2013.01); *C07K 16/18* (2013.01); *G01N 33/577* (2013.01); *G01N 33/57484* (2013.01); *G01N 33/6854* (2013.01); *A61K 2039/505* (2013.01); *C07K 2317/33* (2013.01); *C07K 2317/34* (2013.01); *C07K 2317/565* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,890,531 B1 | 5/2005 | Horie et al. | |
| 8,968,740 B2 | 3/2015 | Shipp et al. | |
| 9,206,427 B2 | 12/2015 | Shipp et al. | |
| 10,519,238 B2 | 12/2019 | Shipp et al. | |
| 2007/0269442 A1 | 11/2007 | Webber et al. | |
| 2009/0191182 A1 | 7/2009 | Shipp et al. | |
| 2010/0080794 A1 | 4/2010 | Tsuji et al. | |
| 2010/0297664 A1 | 11/2010 | Wadhwa et al. | |
| 2011/0065756 A1* | 3/2011 | De Taeye ............ A61K 31/427 514/342 |
| 2013/0011409 A1 | 1/2013 | Shipp et al. | |
| 2013/0065258 A1 | 3/2013 | Watanabe et al. | |

FOREIGN PATENT DOCUMENTS

| | | | |
|---|---|---|---|
| WO | WO-1989/000581 A1 | 1/1989 | |
| WO | WO-8900581 A1 * | 1/1989 | ......... A61K 47/6817 |
| WO | WO-2006/108474 A2 | 10/2006 | |
| WO | WO-2007/126439 A2 | 11/2007 | |
| WO | WO-2011/060272 A2 | 5/2011 | |
| WO | WO-2011/157713 A2 | 12/2011 | |
| WO | WO-2015/013388 A2 | 1/2015 | |
| WO | WO-2015/013389 A2 | 1/2015 | |

OTHER PUBLICATIONS

UniProtKB/Swiss-Prot: Q62529 Beta-galactoside-binding lectin. Nov. 2006. (Year: 2006).*
Gitt et al. Evidence that a human soluble β-galactoside-binding lectin is encoded by a family of genes. Proc. Natl. Acad. Sci. USA vol. 83, pp. 7603-7607, Oct. 1986. (Year: 1986).*
Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," J Protein Chem, 11(5): 433-444 (1992).
Alves et al., "Significance of galectins-1, -3, -4 and -7 in the progression of squamous cell carcinoma of the tongue," Pathology Res. Pract. 207:236-240 (2011).
Chen et al., "PD-L1 Expression Is Characteristic of a Subset of Aggressive B-cell Lymphomas and Virus-Associated Malignancies," Clin. Cancer Res. 19(13):3462-3473 (2013).
Chung et al., "Galectin-1 Promotes Lung Cancer Progression and Chemoresistance by Upregulating p38 MAPK, ERK, and Cyclooxygenase-2," Clin. Cancer Res. 18:4037-4047 (2012).
Chung et al., "Proteomic Analysis to Identify Biomarker Proteins in Pancreatic Ductal Adenocarcinoma," ANZ J. Surg. 78:245-251 (2008).
Colman, "Effects of amino acid sequence changes on antibody-antigen interactions" 145(1):33-36 (1994).
Croci et al., "Disrupting galectin-1 interactions with N-glycans suppresses hypoxia-driven angiogenesis and tumorigenesis in Kaposi's sarcoma," J. Exp. Med. 209:1985-2000 (2012).
Dalotto-Moreno et al., "Targeting Galectin-1 Overcomes Breast Cancer-Associated Immunosuppression and Prevents Metastic Disease," Cancer Res. 73:1107-1117 (2013).
Extended European Search Report from European Patent Application No. 14828887.1 dated Feb. 24, 2017.

(Continued)

*Primary Examiner* — Maher M Haddad
(74) *Attorney, Agent, or Firm* — Foley Hoag LLP

(57) ABSTRACT

The present invention is based, in part, on the discovery of galectin 1 (Gal1) epitopes against which anti-Gal1 agents can neutralize Gal1 function, as well as anti-Gal1 agents and methods useful for neutralizing Gal1 function.

18 Claims, 7 Drawing Sheets
Specification includes a Sequence Listing.

(56) References Cited

OTHER PUBLICATIONS

Extended European Search Report from European Patent Application No. 14829106.5 dated Mar. 30, 2017.
GenBank Accession No. U05693-1. Mus spretus beta-galactoside-binding lectin gene, partial cds and 3' UTR. Feb. 4, 1995, p. 1.
International Search Report dated Jan. 14, 2015 from PCT/US2014/047784.
International Search Report dated Feb. 11, 2015 from PCT/US2014/047783.
Juszczynski et al., "MLL-Rearranged B Lymphoblastic Leukemias Selectively Express the Immunoregulatory Carbohydrate-Binding Protein Galectin-1," Clin. Cancer Res. 16:2122-2130 (2010).
Juszczynski et al., "The AP1-dependent secretion of galactin-1 by Reed-Sternberg cells fosters immune privilege in classical Hodgkin lymphoma," Proc. Natl. Acad. Sci. USA 104:13134-13139 (2007).
Kamper et al., "Proteomic analysis identifies galectin-1 as a predictive biomarker for relapsed/refractory disease in classical Hodgkin lymphoma," Blood 117:6638-6649 (2011).
Laderach et al., "A Unique Galectin Signature in Human Prostate Cancer Progression Suggests Galectin-1 as a Key Target for Treatment of Advanced Disease," Cancer Res. 73:86-96 (2013).
Le et al., "Galectin-1: A Link Between Tumor Hypoxia and Tumor Immune Privilege," J. Clin. Oncol. 23:8932-8941 (2005).
Lederman et al., "A Single Amino Acid Substitution in a Common African Allele of the CD4 Molecule Ablates Binding of the Monoclonal Antibody, OKT4," Mol Immunol, 28(11): 1171-1178 (1991).
Li et al., "beta-Endorphin Omission Analogs: Dissociation of Immunoreactivity from Other Biological Activities," Proc Natl Acad Sci USA, 77(6): 3211-3214 (1980).
Lopez-Lucendo et al., "Growth-regulatory human galectin-1: crystallographic characterisation of the structural changes induced by single-site mutations and their impact on the thermodynamics of ligand binding," J. Mol. Biol. 343:957-970 (2004).
Mathieu et al., "Galectin-1 in Melanoma Biology and Related Neo-Angiogenesis Processes," J. Invest. Dermatol. 132:2245-2254 (2012).
Ouyang et al., "Galectin-1 serum levels reflect tumor burden and adverse clinical features in classical Hodgkin lymphoma," Blood 121:3431-3433 (2013).
Ouyang et al., "Viral induction and targeted inhibition of galectin-1 in EBV$^+$ posttransplant lymphoproliferative disorders," Blood 117:4315-4322 (2011).
Rodig et al., "AP1-Dependent Galectin-1 Expression Delineates Classical Hodgkin and Anaplastic Large Cell Lymphomas from Other Lymphoid Malignancies with Shared Molecular Features," Clin. Cancer Res. 14:3338-3344 (2008).
Rubinstein et al., "Targeted inhibition of galectin-1 gene expression in tumor cells results in heightened T cell-mediated rejection: A potential mechanism of tumor-immune privilege," Cancer Cell 5:241-251 (2004).
Rudikoff et al., "Single amino acid substitution altering antigen-binding specificity," P Natl Acad Sci USA, 79(6):1979-1983 (1982).
Tang et al., "Identification of Galectin-1 as a novel biomarker in nasopharyngeal carcinoma by proteomic analysis," Oncol. Reports 24:495-500 (2010).
Wu et al., "Overexpression of galectin-1 is associated with poor prognosis in human hepatocellular carcinoma following resection," J. Gastroenterol. Hepatol. 27:1312-1319 (2012).

* cited by examiner

8A12H9H10 recognizes endogenous human and murine Gal1 at similar range of titers.

ANTI-GALECTIN-1 (GAL1) MONOCLONAL ANTIBODIES AND FRAGMENTS THEREOF FOR NEUTRALIZING GAL1

BACKGROUND OF THE PRESENT INVENTION

Galectin-1 (Gal1), a member of a highly conserved family of carbohydrate-binding proteins, modulates immune responses and fosters tumor-immune escape through specific recognition of N-acetyllactosamine (Gal-β1-4-NAcGlc) residues on the branches of N- or O-linked glycans (Juszczynski et al. (2007) *Proc Natl Acad Sci USA*. 104:13134-13139; Rabinovich and Croci (2012) *Immunity* 36:322-335; Rabinovich and Toscano (2009) *Nat. Rev Immunol*. 9:338-352; Rubinstein et al. (2004) *Cancer Cell* 5:241-251).

Gal1 selectively induces the apoptosis of cytotoxic T cells and T helper (Th) 1 and Th17 cells by interacting with specifically sialated cell surface glycoproteins, such as CD45, CD43 and CD7 (Toscano et al. (2007) *Nat. Immunol*. 8:825-834). Since Th2 cells and regulatory T (Treg) cells lack the Gal1-binding glycoprotein motif, Gal1 spares these cells and fosters an immunosuppressive Th2/Treg-enriched tumor microenvironment (Toscano et al. (2007) *Nat. Immunol*. 8:825-834). Gal1 also promotes the expansion of regulatory T (Treg) cells (Juszczynski et al. (2007) *Proc Natl Acad Sci USA*. 104:13134-13139; Toscano et al. (2007) *Nat. Immunol*. 8:825-834) and Gal1-glycan interactions augment hypoxia-driven tumor angiogenesis (Croci et al. (2012) *J. Exp. Med*. 209:1985-2000).

These molecular mechanisms underlie the effect of Gal1 on promoting classical Hodgkin lymphoma (cHL). cHL is a B-cell malignancy diagnosed in approximately 20,000 new patients in North America and Europe each year; >90% of these patients are young adults. cHL include small numbers of malignant Hodgkin Reed-Sternberg (HRS) cells within an extensive Th2/Treg-skewed inflammatory infiltrate (Küppers et al. (2002) *Ann. Oncol*. 13:11-18; Juszczynski et al. (2007) *Proc Natl Acad Sci USA*. 104:13134-13139; Küppers (2009) *Nat. Rev. Cancer* 9:15-27). HRS cells overexpress Gal1, which selectively kills Th1 and cytotoxic T cells and promotes the immunosuppressive Th2/Treg-predominant HL microenvironment (Juszczynski et al. (2007) *Proc Natl Acad Sci USA*. 104:13134-13139). HRS cells lack B-cell receptor-mediated signals and rely on alternative survival and proliferative pathways activated by transcription factors, such as NF-κB and activator protein 1 (AP1) (Küppers et al. (2002) *Ann. Oncol*. 13:11-18; Mathas et al. (2002) *EMBO J*. 21:4104-4113; Schwering et al. (2003) *Mol. Med*. 9:85-95). In cHL, the tumor cells exhibit constitutive AP1 activation, express high levels of the AP1 components, cJun and Jun B, and depend on AP1-mediated proliferation signals (Mathas et al. (2002) *EMBO J*. 21:4104-4113; Juszczynski et al. (2007) *Proc Natl Acad Sci USA*. 104:13134-13139; Rodig et al. (2008) *Clin. Cancer Res*. 14:3338-3344). Although primary cHLs have a brisk inflammatory infiltrate, there is little evidence of an effective host antitumor immune response. The reactive T cell population included predominantly Th2-type and CD4+CD25hiFoxP3+ regulatory T cells that directly suppress immune responses and protect HRS cells from immune attack (Re et al. (2005) *J. Clin. Oncol*. 23:6379-6386; Marshall et al. (2004) *Blood* 103:1755-1762; Gandhi et al. (2006) *Blood* 108:2280-2289). Th1 and natural killer and cytotoxic T cells are markedly underrepresented.

Increased Gal1 expression in immunohistochemical analyses of primary cHLs is associated with poorer event-free survival (Kamper et al. (2011) *Blood* 117:6638-6649). In particular, elevated serum Gal1 levels are significantly associated with tumor burden and adverse clinical features in newly diagnosed patients with cHL (Ouyang et al. (2013) *Blood* 121:3431-3433). Moreover, Gal1 expression is also associated with EBV-associated post-transplant lymphoproliferative disorder (PTLD) (Gottschalk et al. (2005) *Annu. Rev. Med*. 56:29-44; Ouyang et al. (2011) *Blood* 117:4165-4166 and 4315-4322), MLL-rearranged ALL (Juszczynski et al. (2010) *Clin. Cancer Res*. 16:2122-2130), and Kaposi's sarcoma (Tang et al. (2010) *Oncol. Rep*. 24:495-500). In addition to these select lymphoid malignancies and virally induced cancers, Gal1 is also expressed by many solid tumors, including breast cancer (Croci et al. (2012) *J. Exp. Med*. 209:1985-2000), prostate cancer (Dalotto-Moreno et al. (2013) *Cancer Res*. 73:1107-1117), lung cancer (Laderach et al. (2013) *Cancer Res*. 73:86-96), pancreatic cancer (Chung et al. (2012) *Clin. Cancer Res*. 18:4037-4047), squamous cell carcinoma of the head and neck (Chung et al. (2008) *ANZ J. Surg*. 78:245-251; Alves et al. (2011) *Pathol. Res. Pract*. 207:236-240), hepatocellular carcinoma (Le et al. (2005) *J. Clin. Oncol*. 23:8932-41), nasopharyngeal carcinoma (Wu et al. (2012) *J. Gastroenterol. Hepatol*. 27:1312-1319), and melanoma (Rubinstein et al. (2004) *Cancer Cell* 5:241-251; Mathieu et al. (2012) *J. Invest. Dermatol*. 132:2245-2254). Gal1 expression has been identified as an adverse prognostic marker in the above-mentioned solid tumors. Moreover, Gal1 silencing is associated with anti-tumor effects in breast cancer (Croci et al. (2012) *J. Exp. Med*. 209:1985-2000), prostate cancer (Dalotto-Moreno et al. (2013) *Cancer Res*. 73:1107-1117), lung cancer (Laderach et al. (2013) *Cancer Res*. 73:86-96), and melanoma (Rubinstein et al. (2004) *Cancer Cell* 5:241-251).

Given the broadly immunosuppressive activities of Gal1, these results suggest that Gal1 is a very powerful target for therapy in many cancers and other disorders mediated by Gal1. In view of the above, it is clear that there remains a need in the art for compositions and methods to effectively neutralize unwanted Gal1 activity.

SUMMARY OF THE PRESENT INVENTION

The present invention relates in general to anti-galectin-1 (Gal1) agents that neutralize Gal1 function based on the identification of specific anti-Gal1 epitopes that are unexpectedly effective in generating neutralizing Gal1 agents.

In one aspect, a recombinant polypeptide of less than or equal to about 60 amino acids in length comprising an amino acid sequence that is at least 80% identical to an amino acid sequence selected from the group consisting of residues 102-115 of SEQ ID NOs: 2, 4, 6, 8, 10, 12, 14, and 16 is provided. In one embodiment, said polypeptide is equal to 14 amino acids in length. In another embodiment, said amino acid sequence is identical to the amino acid sequence of residues 102-115 of any one of SEQ ID NOs: 2, 4, 6, 8, 10, 12, 14, and 16. In another embodiment, said polypeptide further comprises a heterologous sequence. In still another embodiment, the polypeptide is isolated. In yet another embodiment, said polypeptide is covalently linked to a detectable label. In another embodiment, said polypeptide is covalently bonded to a carrier molecule or immobilized on an object (e.g., an object selected from the group consisting of a cell, a metal, a resin, a polymer, a ceramic, a glass, a microelectrode, a graphitic particle, a bead, a gel, a plate, an array, and a capillary tube).

In another aspect, a recombinant nucleic acid molecule having a sequence that hybridizes under stringent conditions with the complement of a nucleic acid encoding a polypeptide of the present invention described herein or having a sequence with at least about 95% homology to a nucleic acid encoding a polypeptide of the present invention described herein, wherein the nucleic acid molecule is only as long as required to encode the polypeptide is provided.

In still another aspect, a vector comprising a recombinant nucleic acid of the present invention described herein, optionally wherein the vector is an expression vector comprising a promoter to which the nucleic acid is operably linked, is provided.

In yet another aspect, a host cell which expresses a polypeptide of the present invention described herein, comprises a nucleic acid of the present invention described herein, or comprises a vector of the present invention described herein, is provided.

In another aspect, an immunogenic composition comprising a polypeptide of the present invention described herein, a nucleic acid of the present invention described herein, a vector of the present invention described herein, or a host cell of the present invention described herein; and a pharmaceutically acceptable carrier, are provided. In one embodiment, the immunogenic composition further comprises at least one additional immunostimulatory agent (e.g., an adjuvant and/or an immune checkpoint inhibitor). In still another embodiment, the immune checkpoint is selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof. In yet another embodiment, the immunogenic composition is capable of eliciting neutralizing anti-Gal1 antibodies in mammals.

In still another aspect, an isolated neutralizing anti-Gal1 antibody, or antigen binding portion thereof, that specifically binds to a polypeptide of the present invention described herein, is provided. In one embodiment, the antibody, or antigen binding portion thereof, is a monoclonal antibody, polyclonal antibody, chimeric antibody, humanized antibody, single-chain antibody, antibody fragment, composite, murine, human, or is detectably labeled. In another embodiment, the antibody, or antigen-binding fragment thereof, is detectably labeled, comprises an effector domain, comprises an Fc domain, and/or is selected from the group consisting of Fv, Fav, F(ab')2), Fab', dsFv, scFv, sc(Fv)2, and diabodies fragments.

In yet another aspect, a method of identifying a neutralizing anti-Gal1 antibody comprising (a) administering an effective amount of an agent selected from the group consisting of a polypeptide of the present invention described herein, a nucleic acid of the present invention described herein, a vector of the present invention described herein, a host cell of the present invention described herein, or an immunogenic composition of the present invention described herein, to a subject to generate antibodies that neutralize Gal1; and (b) isolating anti-Gal1 antibodies specific for the administered agent, is provided.

In another aspect, a method of identifying a neutralizing anti-Gal1 antibody comprising (a) administering an effective amount of an agent selected from the group consisting of a polypeptide of the present invention described herein, a nucleic acid of the present invention described herein, a vector of the present invention described herein, a host cell of the present invention described herein, or an immunogenic composition of the present invention described herein, to B cells in an in vitro cell culture system to generate antibodies that neutralize Gal1; and (b) isolating anti-Gal1 antibodies specific for the administered agent, is provided.

In still another aspect, a method of making an isolated hybridoma which produces a neutralizing anti-Gal1 antibody that specifically binds to Gal1 comprising: a) immunizing a mammal with or contacting B cells with an effective amount of an agent selected from the group consisting of a polypeptide of the present invention described herein, a nucleic acid of the present invention described herein, a vector of the present invention described herein, a host cell of the present invention described herein, or an immunogenic composition of the present invention described herein; b) optionally isolating splenocytes from the immunized mammal; c) fusing splenocytes from the immunized mammal or B cells with an immortalized cell line to form hybridomas; and d) screening individual hybridomas for production of an anti-Gal1 antibody which specifically binds with the agent, is provided.

In yet another aspect, an antibody produced by a method of the present invention described herein, is provided.

In another aspect, a method of eliciting an anti-Gal1 immune response in a subject comprising administering to the subject a prophylactically or therapeutically effective amount of an agent selected from the group consisting of a polypeptide of the present invention described herein, a nucleic acid of the present invention described herein, a vector of the present invention described herein, a host cell of the present invention described herein, an immunogenic composition of the present invention described herein, or an antibody of the present invention described herein, to thereby elicit the immune response, is provided. In one embodiment, the agent is administered in a single dose, administered in multiple doses, or is administered as part of a heterologous prime-boost regimen.

In still another aspect, a method of inhibiting Gal1 activity in a subject comprising administering to the subject a prophylactically or therapeutically effective amount of an agent selected from the group consisting of a polypeptide of the present invention described herein, a nucleic acid of the present invention described herein, a vector of the present invention described herein, a host cell of the present invention described herein, an immunogenic composition of the present invention described herein, or an antibody of the present invention described herein, thereby inhibiting Gal1 activity in the subject, is provided.

In yet another aspect, a method for preventing or delaying the onset of, or slowing the rate of progression of, a disease in a subject mediated by Gal1 activity, comprising administering to the subject a prophylactically or therapeutically effective amount of an agent selected from the group consisting of a polypeptide of the present invention described herein, a nucleic acid of the present invention described herein, a vector of the present invention described herein, a host cell of the present invention described herein, an immunogenic composition of the present invention described herein, or an antibody of the present invention described herein, thereby preventing or delaying the onset of, or slowing the rate of progression of, the Gal1-mediated disease in the subject, is provided.

Certain embodiments can be applied to any method of the present invention described herein. For example, the method can further comprise administering at least one additional agent that upregulates an immune response. In another embodiment, the at least one additional agent comprises an inhibitor of an immune checkpoint. In still another embodiment, the immune checkpoint is selected from the group consisting of PD-1, PD-L1, PD-L2, LAG-3, TIM-1, CTLA- 4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof. In yet another embodiment, the Gal1-mediated disease is a Gal1-positive cancer, Gal1-mediated angiogenesis disorder, AP1-dependent lymphoid malignancies, MLL-rearranged ALL, EBV+ post-transplant lymphoproliferative disorder (PTDL), nasopharyngeal carcinoma, Kaposi's sarcoma, breast cancer, prostate cancer, lung cancer, pancreatic cancer, squamous cell carcinoma of the head and neck, hepatocellular carcinoma, and melanoma. In another embodiment, the subject is a mammal. In still another embodiment, the mammal is a human.

DETAILED DESCRIPTION OF THE PRESENT INVENTION

Figure 1:
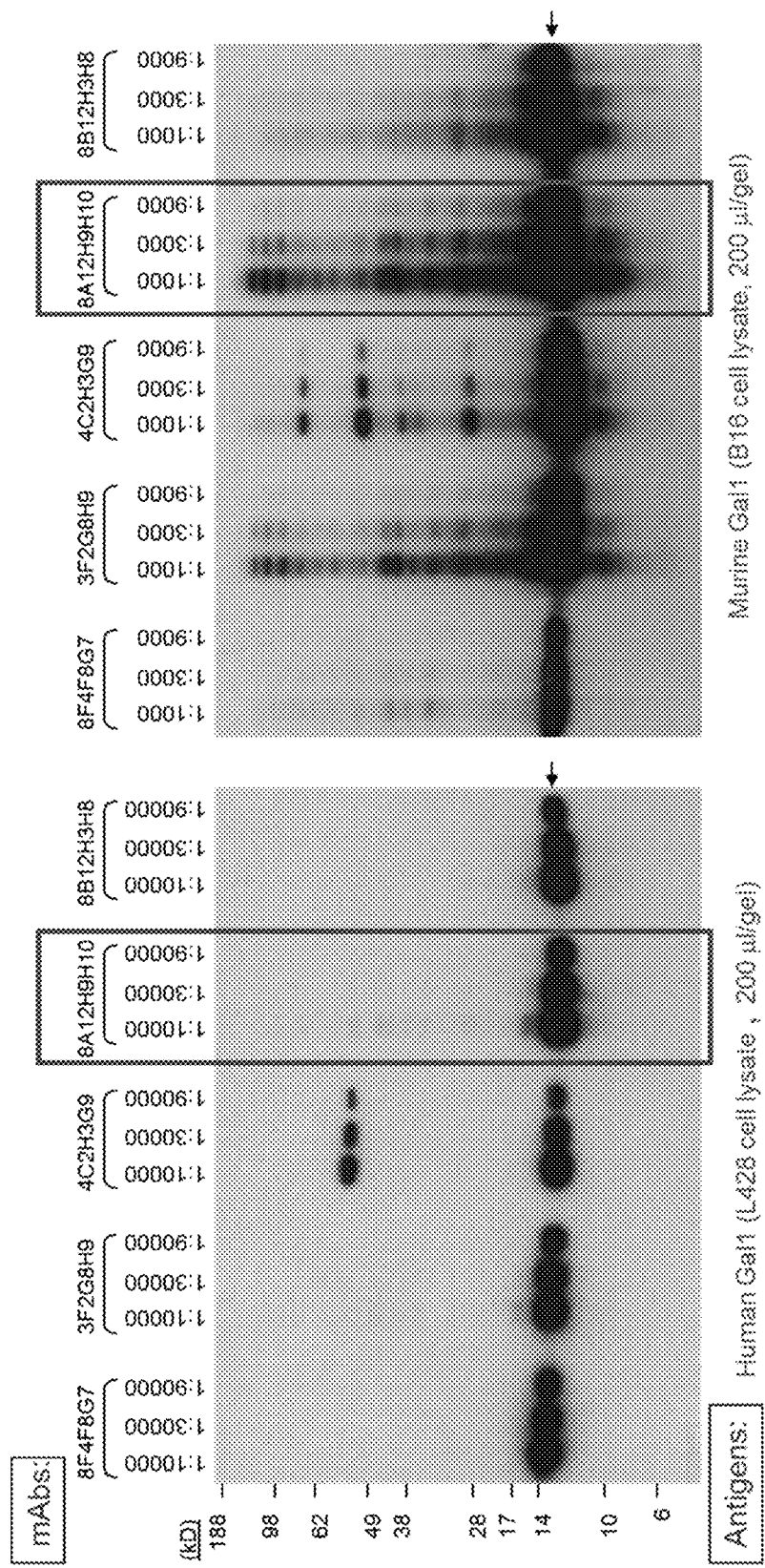
FIG. 1 shows cross-reactivity of anti-Gal1 monoclonal antibody, 8A12, on endogenous human and murine Gal1 on Western-blot (WB). WB analysis of cell lysates derived from human Hodgkin lymphoma line, L428 and murine melanoma line, B16-F10. Lysates were probed with 8A12 at different titration showing a specific band of Gal1 (~14 kDa). 8A12 recognizes endogenous human and murine Gal1 at similar range of titres.

The present invention is based in part on the discovery of galectin 1 (Gal1) epitopes against which anti-Gal1 agents can neutralize Gal1 function, as well as anti-Gal1 agents and methods useful for neutralizing Gal1 function.

I. Definitions

The articles "a" and "an" are used herein to refer to one or to more than one (i.e. to at least one) of the grammatical object of the article. By way of example, "an element" means one element or more than one element.

The term "adjuvants" refers to any agent suitable for enhancing the immunogenicity of an antigen, such as protein and nucleic acid. Adjuvants suitable for use with protein-based immunogens are well known in the art and include, but are not limited to, alum, Freund's incomplete adjuvant (FIA), Saponin, Quil A, QS21, Ribi Detox, Monophosphoryl lipid A (MPL), and nonionic block copolymers such as L-121 (Pluronic; Syntex SAF). Methods of combining adjuvants with antigens are well known to those skilled in the art. Adjuvants can also be in particulate form. The antigen can be incorporated into biodegradable particles composed of poly-lactide-co-glycolide (PLG) or similar polymeric material. Such biodegradable particles are known to provide sustained release of the immunogen and thereby stimulate long-lasting immune responses to the immunogen. Other particulate adjuvants, include but are not limited to, micellular mixtures of Quil A and cholesterol known as immunostimulating complexes (ISCOMs) and aluminum or iron oxide beads. It is also known to those skilled in the art that cytotoxic T lymphocyte and other cellular immune responses are elicited when protein-based immunogens are formulated and administered with appropriate adjuvants, such as ISCOMs and micron-sized polymeric or metal oxide particles. Suitable adjuvants for nucleic acid-based vaccines include, but are not limited to, Quil A, interleukin-12 delivered in purified protein or nucleic acid form, short bacterial immunostimulatory nucleotide sequence, such as CpG-containing motifs, interleukin-2/Ig fusion proteins delivered in purified protein or nucleic acid form, oil in water microemulsions such as MF59, polymeric microparticles, cationic liposomes, monophosphoryl lipid A (MPL), immunomodulators such as Ubenimex, and genetically detoxified toxins such as *E. coli* heat labile toxin and cholera toxin from Vibrio. Such adjuvants and methods of combining adjuvants with antigens are well known to those skilled in the art. In addition, methods for combining antigens and particulate adjuvants are well known to those skilled in the art.

The term "Gal1-mediated disorder" refers to any condition characterized by aberrant or otherwise unwanted Gal1 expression. Exemplary Gal1-mediated disorders include, without limitation, cancer, angiogenesis, hypoxia-associated angiogenesis, and post-transplantation lymphoproliferative disorder. Galectin-1 (Gal1) protein expression and transcript abundance are highly correlated (Juszczynski et al. (2007) *Proc. Natl. Acad. Sci. U.S.A.* 104:13134-13139; Ouyang et al. (2011) *Blood* 117:4315-4322 and accompanying editorial in Blood (2011) 4317:4165-4166). Gal1 is expressed by multiple tumor types, including select lymphoid malignancies, virally induced cancers and many solid tumors.

For example, lymphoid malignancies include, but are not limited to, AP1-dependent lymphoid malignancies such as classical Hodgkin lymphoma (cHL) and anaplastic large cell lymphoma (Juszczynski et al. (2007) *Proc. Natl. Acad. Sci. U.S.A.* 104:13134-13139; Rodig et al. (2008) *Clin. Cancer Res.* 14:3338-3344). Gal1 is a prognostic marker in cHL (Kamper et al. (2011) *Blood* 117:6638-6649). Gal1 also mediates MLL-rearranged ALL. In a comprehensive study, all 32 primary MLL-rearranged ALLs were Gal1+, regardless of translocation partner, whereas only 2/81 germline MLL ALLs expressed Gal1 (Juszczynski et al. (2010) *Clin. Cancer Res.* 16:2122-2130). MLL-rearranged ALL is a poor prognosis disease that requires different treatment (Juszczynski et al. (2010) *Clin. Cancer Res.* 16:2122-2130).

Gal1-mediated virally induced malignancies include, but are not limited to, EBV+ post-transplant lymphoproliferative disorder (PTLD) (Ouyang et al. (2011) *Blood* 117:4315-4322 and accompanying editorial in Blood (2011) 4317: 4165-4166), nasopharyngeal carcinoma (Tang et al. (2010) *Oncol. Rep.* 24:495-500), and Kaposi's sarcoma (Croci et al. (2012) *J. Exp. Med.* 209:1985-2000).

Gal1-mediated solid turmos include, but are not limited to, breast cancer (Dalotto-Moreno et al. (2013) *Cancer Res.* 73:1107-1117), prostate cancer (Laderach et al. (2013) *Cancer Res.* 73:86-96), lung cancer (Chung et al. (2012) *Clin. Cancer Res.* 18:4037-4047), pancreatic cancer (Chung et al. (2008) *ANZ J. Surg.* 78:245-251), squamous cell carcinoma of the head and neck (Alves et al. (2011) *Pathol. Res. Pract.* 207:236-240; Le et al. (2005) *J. Clin. Oncol.* 23:8932-8941), hepatocellular carcinoma (Wu et al. (2012) *J. Gastroenterol.*

Hepatol. 27:1312-1319), and melanoma (Mathieu et al. (2012) *J. Invest. Dermatol.* 132:2245-2254; Rubinstein et al. (2004) *Cancer Cell* 5:241-251). Gal1 expression is also an adverse prognostic marker in all of the above-mentioned solid tumors and Gal1 silencing is associated with anti-tumor effects in breast (Dalotto-Moreno et al. (2013) *Cancer Res.* 73:1107-1117), prostate (Laderach et al. (2013) *Cancer Res.* 73:86-96), and lung (Chung et al. (2012) *Clin. Cancer Res.* 18:4037-4047) cancer and melanoma (Rubinstein et al. (2004) *Cancer Cell* 5:241-251). Moreover, Gal1 transcripts are increased in multiple types of cancers.

The term "angiogenesis" or "neovascularization" refers to the process by which new blood vessels develop from pre-existing vessels (Varner et al. (1999) *Angiogen.* 3:53-60; Mousa et al. (2000) *Angiogen. Stim. Inhib.* 35:42-44; Kim et al. (2000) *Amer. J. Path.* 156:1345-1362; Kim et al. (2000) *J. Biol. Chem.* 275:33920-33928; Kumar et al. (2000) Angiogenesis: From Molecular to Integrative Pharm. 169-180). Endothelial cells from pre-existing blood vessels or from circulating endothelial stem cells (Takahashi et al. (1995) *Nat. Med.* 5:434-438; Isner et al. (1999) *J. Clin. Invest.* 103:1231-1236) become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

For example, the term "tissue exhibiting angiogenesis" refers to a tissue in which new blood vessels are developing from pre-existing blood vessels.

As used herein, the term "inhibiting angiogenesis," "diminishing angiogenesis," "reducing angiogenesis," and grammatical equivalents thereof refer to reducing the level of angiogenesis in a tissue to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis. The level of angiogenesis may be determined using methods well known in the art, including, without limitation, counting the number of blood vessels and/or the number of blood vessel branch points, as discussed herein and in the examples. An alternative in vitro assay contemplated includes the tubular cord formation assay that shows growth of new blood vessels at the cellular level [D. S. Grant et al., Cell, 58: 933-943 (1989)]. Art-accepted in vivo assays are also known, and involve the use of various test animals such as chickens, rats, mice, rabbits and the like. These in vivo assays include the chicken chorioallantoic membrane (CAM) assay, which is suitable for showing anti-angiogenic activity in both normal and neoplastic tissues (Ausprunk (1975) *Amer. J. Path.* 79:597-610 and Ossonowski and Reich (1980) *Cancer Res.* 30:2300-2309). Other in vivo assays include the mouse metastasis assay, which shows the ability of a compound to reduce the rate of growth of transplanted tumors in certain mice, or to inhibit the formation of tumors or preneoplastic cells in mice which are predisposed to cancer or which express chemically-induced cancer (Humphries et al. (1986) *Science* 233:467-470 and Humphries et al. (1988) *J. Clin. Invest.* 81:782-790). Moreover, in some embodiments, angiogenesis can be measured according to such attributes as pericyte maturation and vascular remodeling as described further herein.

As used herein, the term "hypoxia associated angiogenesis" or "hypoxia-induced angiogenesis" refers generally to the process of pathological angiogenesis in non-neoplastic disease states and is typically, although not necessarily, accompanied by a transition to a neoplastic state. Hypoxia-induced transcription factors (HIFs) induce the expression of angiogenic factors including HIF-1zlpha, VEGF, nitric oxide synthase, PDFG, Ang2, and others. As a result, hypoxia associated angiogenesis encompasses a well-known set of pathological conditions characterized by such a process Pugh et al. (2003) *Nat Med* 9, 677-684; Fraisl et al. (2009) *Dev Cell* 16, 167-179;Ferrara et al. (2005) *Nature* 438, 967-974; Ferrara (2010) *Cytokine Growth Factor Rev* 21, 21-26]. In some embodiments, the set of hypoxia associate angiogenesis pathologies includes, but is not limited to, neoplasms and cancers, age-related macular degeneration, diabetes retinopathy, atherosclerosis, chronic obstructive lung disease, and psoriasis.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., Gal1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention bind specifically or substantially specifically to Gal1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. In another embodiment, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The term "effective amount" refers to an amount sufficient to achieve a desired result. For example, a "prophylactically effective amount" refers to an amount sufficient to reduce the likelihood of a disorder from occurring. In addition, a "therapeutically effective amount" refers to an amount effective to slow, stop or reverse the progression of a disorder.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, "framework" or "FR" residues are those variable-domain residues other than the HVR residues as herein defined.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like) Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune cell" refers to cells that play a role in the immune response Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune checkpoints" means a group of molecules on the cell surface of CD4+ and CD8+ T cells. These molecules fine-tune immune responses by down-modulating or inhibiting an anti-tumor immune response Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, and A2aR (see, for example, WO 2012/177624) Immunotherapeutic agents that can act as immune checkpoint inhibitors useful in the methods of the present invention, include, but are not limited to, blocking antibodies for any one or more immune checkpoints.

As used herein, the term "immune disorder" includes immune diseases, conditions, and predispositions to, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, or MLL$^+$ pre B-cell ALL), cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

The term "immunizing" refers to generating an immune response to an antigen in a subject. This can be accomplished, for example, by administering a primary dose of an immunogen to a subject, followed after a suitable period of time by one or more subsequent administrations of the immunogen, so as to generate in the subject an immune response against the immunogen. A suitable period of time between administrations of the immunogen can readily be determined by one skilled in the art, and is usually on the order of several weeks to months.

As used herein, the term "inhibit" or "neutralize" includes the decrease, limitation, or blockage, of, for example a particular action, function, or interaction. For example, a Gal1-mediated infection or disease is "inhibited" if at least one symptom of the disease, such as immune function, is modulated in a desirable manner. As used herein, a Gal1-mediated infection or disease is also "inhibited" if recurrence of a disease symptom is reduced, slowed, delayed, or prevented. For example, a Gal1-mediated activity can be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more. The term "promote," in some embodiments, can be used in the exact opposite manner as "inhibit."

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term an "isolated antibody" is intended to refer to an antibody which is substantially free of other antibodies having different antigenic specificities (e.g., an isolated antibody that specifically binds to human Gal1 and is substantially free of antibodies that do not bind to Gal1). An isolated antibody that specifically binds to an epitope of human Gal1 may, however, have cross-reactivity to other Gal1 proteins, respectively, from different species. However, in some embodiments, the antibody maintains higher affinity and selectivity for human Gal1. In addition, an isolated antibody is typically substantially free of other cellular material and/or chemicals. In one embodiment of the present invention, a combination of "isolated" monoclonal antibodies having different specificities to human Gal1 are combined in a well-defined composition.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a target polypeptide (e.g., immunoglobulin) or fragment thereof, in which the protein is separated from cellular components of the cells from which it is isolated or recombinantly produced. In one embodiment, the language "substantially free of cellular material" includes preparations of target protein or fragment thereof, having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the present invention. The kit may be promoted, distributed, or sold as a unit for performing the methods of the present invention.

The terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "not substantially altered," "not substantially modulated," and the like, unless otherwise defined, refers to a minimal deviation of a measured attribute in comparison to a reference control. The deviation can be measured according to quantitative or qualitative means. In one embodiment, the attribute's alteration is less than 30%, 29%, 28%, 27%, 26%, 25%, 24%, 23%, 22%, 21%, 20%, 19%, 18%, 17%, 16%, 15%, 10%, 9%, 8%, 7%, 6%, 5%, 4%, 2%, 1% or less different relative to the control (e.g., inter-residue differences, angles-of-approach, affinity for antibody binding, etc.).

A "post-transplantation lymphoproliferative disorder", "PTLD", and/or "viral-associated PTLD" each refers to a disorder in which lymphocytes, which are white blood cells produced in the lymphatic tissue (e.g., lymph nodes, spleen, and/or thymus), are over-produced or act abnormally and are caused by or correlated with a virus. Lymphoid cells include thymus derived lymphocytes (T cells); bone marrow-derived lymphocytes (B cells), and natural killer (NK cells), for example. Lymphocytes progress through a number of different stages, including proliferation, activation, and maturation, and lymphoma or aberrant proliferation can develop at each stage. Disorders may be malignant neoplasms (and may be classified as aggressive or indolent, or as low, intermediate or high-grade), including those associated with IFN-.gamma., or the disorders may involve non-malignant aberrant expansion of lymphoid cells. LPDs include any monoclonal or polyclonal LPD that is not resolving without treatment and/or that involves excessive cellular proliferation, such as an expanding, monoclonal, polyclonal or oligoclonal, lymphoid neoplasm. Cellular proliferation may be more rapid than normal and may continue after the stimuli that initiated the new growth cease. A neoplasm will show partial or complete lack of structural organization and functional coordination with the normal tissue, and may form a distinct mass of tissue that may be either benign (benign tumor) or malignant (cancer).

Such viral-associated PTLD may be caused by or associated with, e.g., Epstein-Barr virus (EBV), a herpes virus, HHV-8, cytomegalovirus, C-type retrovirus, human T-lymphotropic virus type 1 (C-type retrovirus), and/or human immunodeficiency virus (HIV, HIV-1, HIV-2). HIV- and/or AIDS-associated cancers include HIV-associated LPDs, such as Karposi sarcoma, non-Hodgkin's lymphoma, central nervous system (CNS) lymphoma, adult T-cell leukemia/lymphoma (HTLV-1+), and AIDS-associated lymphoma Immune deficiency such as in AIDS patients, organ transplant recipients, and genetic immune disorders may allow latent EBV to reactivate, causing proliferation of abnormal lymphocytes and the potential to develop an EBV-associated LPD, for example. Methods to detect the presence of virus or viral infection in an aberrant cell, such as a cell involved in a PTLD, are known in the art. Viral nucleic acids or polypeptides may be detected in a cell, tissue, or organism such as an aberrant cell, for example. Also, methods to detect immune response specific for a virus are known. A delayed type-hypersensitivity (DTH) assay, such as a trans vivo DTH assay may be used to detect regulatory T cells, for example. In such an assay, human or other mammalian peripheral blood mononuclear cells (PBMC) may be mixed with a carrier control with and without viral antigen, for example, and injected into a heterologous naive recipient, such as the pinnae or footpad of naive mice. If the donor of the PBMC had previously been sensitized to the challenge antigen, DTH-like swelling responses are observed.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a viral-associated PTLD. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to Gal1, is intended to refer to a nucleic acid molecule in which the nucleotide sequences encoding the antibody or antibody portion are free of other nucleotide sequences encoding antibodies or antibody portions that bind antigens other than Gal1, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 56, 57, 58, 59, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long, or less than such amino acids in length, or any range in between, inclusive, so long as they are less than the length of the full-length polypeptide. Alternatively, they can be no longer than and/or excluding such a range so long as they are less than the length of the full-length polypeptide. The range can also include a polypeptide domain of interest, such as the F5 beta strand domain of Gal1, which is well known in the art and is between 55 and 59 amino acids in length.

As used herein, the term "rearranged" refers to a configuration of a heavy chain or light chain immunoglobulin locus wherein a V segment is positioned immediately adjacent to a D-J or J segment in a conformation encoding essentially a complete VH and VL domain, respectively. A rearranged immunoglobulin gene locus can be identified by comparison to germline DNA; a rearranged locus will have at least one recombined heptamer/nonamer homology element.

As used herein, the term "recombinant" refers to biological material, such as a nucleic acid, protein, antibody, cell, and the like, that is manipulated or engineered by the hand of man in order to be made in a non-naturally occurring state. For example, a "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention "response" is generally related to for example, determining the effects on progression, efficacy, or outcome of a clinical intervention. In some embodiments, responses relate directly to a change in tumor mass and/or volume after initiation of clinical intervention (e.g., administration of an anti-Gal1 monoclonal antibody). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human Gal1 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a Gal1-mediated disorder. The term "subject" is interchangeable with "patient". The term "non-human animal" includes all vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, word-length=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, F. Ausubel, et al., ed. Current Protocols in Molecular Biology, Greene Publishing and Wiley Interscience, New York (1987)).

Before the present invention is further described, it will be appreciated that specific sequence identifiers (SEQ ID NOs) have been referenced throughout the specification for purposes of illustration and should therefore not be construed to be limiting. Any marker of the present invention, including, but not limited to, the markers described in the specification and markers described herein are well known in the art and can be used in the embodiments of the present invention.

It is further to be understood that this invention is not limited to particular embodiments described, as such can, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a polypeptide" includes a plurality of polypeptides and reference to "the active agent" includes reference to one or more active agents and equivalents thereof known to those skilled in the art, and so forth. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

II. Polypeptides, Antibodies, and Immunogenic Compositions

The present invention relates, in part, to Gal1 epitopes useful as targets for neutralizing Gal1 activity. Such epitopes can be used to isolated agents, such as antibodies or fragments thereof, that are directed against Gal1 and neutralize Gal1 activity. Such molecules are characterized in that they exhibit an unexpected ability to neutralize Gal1 protein function based on structure-function relationships described further in the Examples below.

Sequences, structures, domains, biophysical characteristics, and functions of Gal1 gene and gene products have been described in the art. See, for example, Rabinovich et al. (2002) *Trends Immunol.* 23:313-320; Liu and Rabinovich (2005) *Nat. Rev. Cancer* 5:29-41; Rubinstein et al. (2004) *Cancer Cell* 5:241-251; Le et al. (2005) *J. Clin. Oncol.* 23:8932-8941; Vasta et al. (2004) *Curr Opin Struct Biol* 14:617-630; Toscano et al. (2007) *Cyt. Growth Fact. Rev.* 18:57-71; Camby et al. (2006) *Glycobiol.* 16:137R-157R; U.S. Pat. Publs. 2003-0004132, 2003-0109464, 2006-0189514, 2009-0176223, 2009-0191182, 2012-0028825, and 2013-0011409, each of which is incorporated herein, by reference, in its entirety. The nucleic acid and amino acid sequences of a representative human Gal1 biomarker is available to the public at the GenBank database under NM_002305.3 and NP_002296.1. Nucleic acid and polypeptide sequences of Gal1 orthologs in organisms other than humans are well known and include, for example, monkey Gal1 (NM_001168627.1 and NP_001162098.1), chimpanzee Gal1 (XM_003953882.1 and XP_003953931.1; XM_003953883.1 and XP_003953932.1; XM_001162104.3 and XP_001162104.1), mouse Gal1 (NM_008495.1 and NP_032521.1), rat Gal1 (NM_019904.1 and NP_063969.1), dog Gal1 (NM_001201488.1 and NP_001188417.1), chicken Gal1 (NM_206905.1 and NP_996788.1), and cow Gal1 (NM_175782.1 and NP_786976.1). For example, relevant Gal1 sequences useful for detection include those listed below in Table 3:

TABLE 3

```
SEQ ID NO. 1: Human Gal1 cDNA Sequence
   1    atggcttgtg gtctggtcgc cagcaacctg aatctcaaac ctggagagtg ccttcgagtg 61    cgaggcgagg tggctcctga cgctaagagc ttcgtgctga acctgggcaa agacagcaac 121    aacctgtgcc tgcacttcaa ccctcgcttc aacgcccacg gcgacgccaa caccatcgtg 181    tgcaacagca aggacggcgg ggcctggggg accgagcagc gggaggctgt ctttcccttc 241    cagcctggaa gtgttgcaga ggtgtgcatc accttcgacc aggccaacct gaccgtcaag 301    ctgccagatg gatacgaatt caagttcccc aaccgcctca acctggaggc catcaactac 361    atggcagctg acggtgactt caagatcaaa tgtgtggcct ttgactga SEQ ID NO. 2: Human Gal1 Amino Acid Sequence
   1    macglvasnl nlkpgeclrv rgevapdaks fvlnlgkdsn nlclhfnprf nahgdantiv 61    cnskdggawg teqreavfpf qpgsvaevci tfdqanltvk lpdgyefkfp nrlnleainy 121    maadgdfkik cvafd SEQ ID NO. 3: Mouse Gal1 cDNA Sequence
   1    atggcctgtg gtctggtcgc cagcaacctg aatctcaaac ctggggaatg tctcaaagtt 61    cggggagagg tggcctcgga cgccaagagc tttgtgctga acctgggaaa agacagcaac 121    aacctgtgcc tacacttcaa tcctcgcttc aatgccatg gagacgccaa caccattgtg 181    tgtaacacca aggaagatgg gacctgggga accgaacacc gggaacctgc cttcccttc 241    cagcccggga gcatcacaga ggtgtgcatc acctttgacc aggctgacct gaccatcaag 301    ctgccagacg gacatgaatt caagttcccc aaccgcctca acatggaggc catcaactac 361    atggcggcgg atggagactt caagattaag tgcgtggcct ttgagtga SEQ ID NO. 4: Mouse Gal1 Amino Acid Sequence
   1    macglvasnl nlkpgeclkv rgevasdaks fvlnlgkdsn nlclhfnprf nahgdantiv 61    cntkedgtwg tehrepafpf qpgsitevci tfdqadltik lpdghefkfp nrlnmeainy 121    maadgdfkik cvafe SEQ ID NO. 5: Monkey Gal1 cDNA Sequence
   1    atggcttgtg gtctggtcgc cagcaacctg aatctcaaac ctggagagtg cctccgagtg 61    cggggcgagg tggcccccga cgccaagagc ttcgtgctga acctgggcaa agatagcaac 121    aacctgtgcc tgcacttcaa ccctcgcttc aacgcccacg gcgacgccaa caccatcgtg
```

TABLE 3-continued

```
181    tgcaacagca aggacggtgg ggcctggggg accgagcagc gggaggctgc ctttcctttc 241    cagcctggaa gtgtcgcaga ggtgtgcatc acctttgacc aggccgacct gaccatcaag 301    ctgccagatg gatacgaatt caagttcccc aaccgcctca acctggaggc catcaactac 361    atggcagctg acggtgactt caagatcaag tgtgtggcct ttgactga SEQ ID NO. 6: Monkey Gal1 Amino Acid Sequence
  1    macglvasnl nlkpgeclrv rgevapdaks fvlnlgkdsn nlclhfnprf nahgdantiv 61    cnskdggawg teqreaafpf qpgsvaevci tfdqadltik lpdgyefkfp nrlnleainy 121    maadgdfkik cvafd SEQ ID NO. 7: Chimpanzee Gal1 cDNA Sequence
  1    atggcttgtg gtctggtcgc cagcaacctg aatctcaaac ctggagagtg ccttcgagtg 61    cgaggcgagg tggcccctga cgctaagagc ttcgtgctga acctgggcaa agacagcaac 121    aacctgtgcc tgcacttcaa ccctcgcttc aacgcccacg gcgacgccaa caccatcgtg 181    tgcaacagca aggacggcgg ggcctggggg accgagcagc gggaggctgt ctttcccttc 241    cagcctggaa gtgttgcaga ggtgtgcatc accttcgacc aggccaacct gaccgtcaag 301    ctgccagatg gatacgaatt caagttcccc aaccgcctca acctggaggc catcaactac 361    atggcagctg acggtgactt caagatcaag tgtgtggcct ttgactga SEQ ID NO. 8: Chimpanzee Gal1 Amino Acid Sequence
  1    macglvasnl nlkpgeclrv rgevapdaks fvlnlgkdsn nlclhfnprf nahgdantiv 61    cnskdggawg teqreavfpf qpgsvaevci tfdqanltvk lpdgyefkfp nrlnleainy 121    maadgdfkik cvafd SEQ ID NO. 9: Rat Gal1 cDNA Sequence
  1    atggcctgtg gtctggtcgc cagcaacctg aatctcaaac ctggggaatg tctcaaagtt 61    cggggagagc tggccccgga cgccaagagc tttgtgttga acctggggaa agacagcaac 121    aacctgtgcc tacacttcaa cccccgcttc aacgcccacg gagatgccaa caccattgtg 181    tgtaacagca aggacgatgg gacctgggga acagaacaac gggagactgc cttccctttc 241    cagcctggga gcatcacgga ggtgtgcatc acctttgacc aggctgacct gaccatcaag 301    ctgccagacg ggcatgaatt caaattcccc aaccgcctca acatggaggc catcaactac 361    atggcggcgg atggtgactt caagattaag tgtgtggcct ttgagtga SEQ ID NO. 10: Rat Gal1 Amino Acid Sequence
  1    macglvasnl nlkpgeclkv rgelapdaks fvlnlgkdsn nlclhfnprf nahgdantiv 61    cnskddgtwg teqretafpf qpgsitevci tfdqadltik lpdghefkfp nrlnmeainy 121    maadgdfkik cvafe SEQ ID NO. 11: Dog Gal1 cDNA Sequence
  1    atggcttgtg gtctggtcgc cagcaatctg agtctcaaac ctgggcagtg cctcagagtg 61    caatgcgagg tggtccccga agccaagagc ttcgtgctga acctgggcaa agacggggac 121    aacctgtgcc tgcacttcaa ccctcgcttt gaagcccatg gcgacgtcaa caccattgtg 181    tgtaacagca aggatggcgg ggcctggggc gaggagcttc gagagtccgc cttcccttc 241    cagcccggga ctgtcacaga ggtgtgcatc tccttcgacc aggctgactt gaccatcaag 301    ctgccagatg gatacaccct caagttcccc aaccgcctca acctggaggc catcagctac 361    ctggcagctg atggtgacat gaagatcaag tgcctggcct ttgactaa
```

TABLE 3-continued

```
SEQ ID NO. 12: Dog Gal1 Amino Acid Sequence
    1   macglvasnl slkpgqclrv qcevvpeaks fvlnlgkdgd nlclhfnprf eahgdvntiv 61   cnskdggawg eelresafpf qpgtvtevci sfdqadltik lpdgytfkfp nrlnleaisy 121   laadgdmkik clafd SEQ ID NO. 13: Chicken Gal1 cDNA Sequence
    1   atggagcaag gactggttgt tacccagctg gatgtacagc ctggagagtg tgtcaaggtc 61   aaagggaaga tcctatccga tgccaaaggg ttttctgtga atgtagggaa ggacagcagc 121   acactcatgc ttcatttcaa ccctcgcttt gactgccatg gggatgtcaa cactgttgtg 181   tgcaactcaa aggaggatgg cacgtggggt gaggaggaca ggaaggctga cttccctttc 241   cagcagggcg acaaggttga gatctgtatc tcctttgatg cagcagaggt caaggtgaag 301   gtgcctgaag tggagtttga gtttcccaat cggctgggca tggagaaaat tcaatacctg 361   gctgtggagg gtgactttaa agtgaaagct attaagttca gctaa SEQ ID NO. 14: Chicken Gal1 Amino Acid Sequence
    1   meqglvvtql dvqpgecvkv kgkilsdakg fsvnvgkdss tlmlhfnprf dchgdvntvv 61   cnskedgtwg eedrkadfpf qqgdkveici sfdaaevkvk vpevefefpn rlgmekiqyl 121   avegdfkvka ikfs SEQ ID NO. 15: Cow Gal1 cDNA Sequence
    1   atggcttgtg gtctggtcgc cagcaacctg aatctcaaac ctggggagtg cctcagagtg 61   cggggcgagg tggccgcaga cgccaagagc ttcttgctga acctgggcaa agacgacaac 121   aacctgtgcc tccacttcaa ccctcgtttc aacgcgcatg gggacgtcaa caccatcgtg 181   tgtaacagca aggacgctgg ggcctggggg gccgagcaga gggaatctgc cttcccttc 241   cagcctggaa gtgtcgtgga ggtatgcatc tccttcaacc agacggacct aaccatcaag 301   ctgcctgatg gatacgaatt caagttcccc aaccgcctca acctggaggc catcaactac 361   ctgtctgcag gtggtgactt caagatcaag tgtgtggcct ttgagtga SEQ ID NO. 16: Cow Gal1 Amino Acid Sequence
    1   macglvasnl nlkpgeclrv rgevaadaks fllnlgkddn nlclhfnprf nahgdvntiv 61   cnskdagawg aeqresafpf qpgsvvevci sfnqtdltik lpdgyefkfp nrlnleainy 121   lsaggdfkik cvafe
```

However, the Gal1 epitopes associated with neutralization of Gal1 epitopes have not been heretofore disclosed. Thus, the present invention provides recombinant and/or isolated Gal1 peptides, or fragments thereof, encompassing Gal1 epitopes against which anti-Gal1 agents can bind and neutralize Gal1 activity. In one aspect, such a Gal1 polypeptide can comprise, consist essentially of, or consist of, a fragment of full-length Gal1 encompassing the entire F5 β-sheet sequence or a portion thereof. In another aspect, a Gal1 polypeptide can comprise, consist essentially of, or consist of, a sequence that is less than or equal to 100, 95, 90, 85, 80, 75, 70, 65, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, or any range in between, that comprises residues 102-115 of any one of SEQ ID NOs: 2, 4, 6, 8, 10, 12, 14, and 16 or an ortholog thereof. In one embodiment of the Gal1 polypeptides of the present invention, the polypeptides can comprise sequences that are at least 50, 55, 60, 65, 70, 75, 80, 85, 90, 91, 92, 93, 94, 95, 96, 97, 98, 99, 99.5, or 100% identical to residues 102-115 of any one of SEQ ID NOs: 2, 4, 6, 8, 10, 12, 14, and 16 or an ortholog thereof. In another embodiment of the Gal1 polypeptides of the present invention, the polypeptides can have 1, 2, 3, 4, 5, 6, 7, 8, 9, 10, 11, 12, 13, 14, 15, 16, 17, 18, 19, or 20 or more conservative amino acid substitutions. In still another embodiment, the present invention provides a composition comprising a recombinant polypeptide described herein and less than about 25%, or alternatively 15%, or alternatively 5%, contaminating biological macromolecules or polypeptides.

In certain embodiments, a polypeptide of the present invention can further comprise a heterologous sequence. For example, fusion proteins are provided containing a domain which increases polypeptide solubility and bioavailability and/or facilitates its purification, identification, detection, and/or structural characterization. In such embodiments, the heterologous portions should not substantially alter the immunogenic activity and/or conformation of the Gal1 neutralizing epitope. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the present invention can comprise one or more heterologous fusions. Polypeptides can contain multiple copies of the same fusion domain or can contain fusions to two or more different domains. The fusions can occur in within the polypeptide as an in-frame insertion, at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide can be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, polypeptides of interest or fragments thereof, are fused to an antibody fragment (e.g., Fc polypeptides). Techniques for preparing these fusion proteins are known, and are described, for example, in WO 99/31241 and in Cosman et. al., 2001 Immunity 14:123 133. Fusion to an Fc polypeptide offers the additional advantage of facilitating purification by affinity chromatography over Protein A or Protein G columns.

In still another embodiment, a polypeptide of interest or fragment thereof can be coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. In vivo techniques for detection of a polypeptide of the present invention include introducing into a subject a labeled antibody directed against the protein. For example, the antibody can be labeled with a radioactive marker whose presence and location in a subject can be detected by standard imaging techniques.

In a particular embodiment, a polypeptide of interest or fragment thereof can be labeled with a fluorescent label to facilitate their detection, purification, or structural characterization. In an exemplary embodiment, a polypeptide of interest or fragment thereof can be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Fragments of the Gal1 neutralizing epitope-containing polypeptides described herein are also provided. For example, deletion or replacement of certain sequences (e.g., the proteolytic cleavage site, signal sequence, and the like) that do not substantially affect the immunogenic activity and/or conformation of the Gal1 neutralizing epitope are contemplated.

Polypeptides of interest or fragments thereof described herein can be produced by recombinant DNA techniques. For example, a nucleic acid molecule encoding the protein is cloned into an expression vector (as described below), the expression vector is introduced into a host cell (as described below) and the protein is expressed in the host cell. The protein of interest can then be isolated from the cells by an appropriate purification scheme using standard protein purification techniques. Alternative to recombinant expression, a protein of interest or fragment thereof can be synthesized chemically using standard peptide synthesis techniques. Moreover, native protein can be isolated from cells (e.g., lymphoma cells), for example, using an antibody (as described below).

In another aspect, polypeptides of the present invention can be used as immunogens to generate neutralizing agents (e.g., antibodies, aptamers, and the like) that bind a Gal1 neutralizing epitope, using standard techniques for polyclonal and monoclonal antibody preparation. The polypeptide or an agent that encodes or produces the polypeptide (e.g., a nucleic acid, vector, host cells, and the like) can be used to prepare antibodies by immunizing a suitable subject, (e.g., human, monkey, rabbit, goat, mouse or other mammal) with the immunogen as further described herein. An appropriate immunogenic preparation can contain, for example, recombinantly expressed protein or a chemically synthesized protein. The preparation can further include an adjuvant, such as Freund's complete or incomplete adjuvant, or similar immunostimulatory agent.

Immunization of a subject with an immunogenic agent described herein induces a polyclonal anti-Gal1 neutralizing antibody response. The polyclonal antibody titer in the immunized subject can be monitored over time by standard techniques, such as with an enzyme linked immunosorbent assay (ELISA) using immobilized target protein. If desired, the antibody molecules directed against a Gal1 neutralizing epitope can be isolated from the mammal (e.g., from the blood) and further purified by well-known techniques, such as protein A chromatography to obtain the IgG fraction. At an appropriate time after immunization, i.e., when the antibody titers of interest are highest, antibody-producing cells can be obtained from the subject and used to prepare monoclonal antibodies.

The term "monoclonal antibody" or "monoclonal antibody composition", as used herein, refers to a population of antibody molecules that contain only one species of an antigen binding site capable of immunoreacting with a particular neutralizing epitope of Gal1. A monoclonal antibody composition thus typically displays a single binding affinity for a particular protein with which it immunoreacts. These can be made using standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an immunogenic agent as described above, and the culture supernatants of the resulting hybridoma cells are screened to identify a hybridoma producing a monoclonal antibody that binds a neutralizing epitope of Gal1.

Any of the many well-known protocols used for fusing lymphocytes and immortalized cell lines can be applied for the purpose of generating an anti-Gal1 neutralizing monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a neutralizing epitope of Gal1, i.e., using a standard ELISA assay.

III. Nucleic Acids, Vectors, and Recombinant Host Cells

A further object of the present invention relates to a nucleic acid sequence encoding Gal1 epitopes associated with neutralizing Gal1 activity, antibodies (e.g., monoclonal antibodies) and fragments thereof, immunoglobulins, and polypeptides of the present invention.

In one embodiment, the present invention provides nucleic acid molecules having a sequence that encodes a peptide or antibody of the present invention. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, a recombinant and/or isolated nucleic acid molecule can contain less than about 5 kb, 4 kb, 3 kb, 2 kb, 1 kb, 0.5 kb or 0.1 kb of nucleotide sequences which naturally flank the nucleic acid molecule in viral DNA. Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention (e.g., disclosed in Table 3 or an ortholog thereof or encodes a polypeptide described herein), can also be a nucleotide sequence which is at least about 50%, preferably at least about 60%, more preferably at least about 70%, yet more preferably at least about 80%, still more preferably at least about 90%, and most preferably at least about 95%, 96%, 97%, 98%, 99% or more identical to such nucleotide sequences, can be engineered and isolated using standard molecular biology techniques and the sequence information provided herein (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, such nucleic acids can be isolated by the polymerase chain reaction using oligonucleotide primers designed based upon sequences described herein or orthologs thereof. For example, RNA or DNA can be isolated from relevant sources containing nucleic acid templates (i.e., by the guanidinium-thiocyanate extraction procedure of Chirgwin et al. (1979) *Biochemistry* 18: 5294-5299) and cDNA can be prepared using reverse transcriptase (i.e., Moloney M L V reverse transcriptase, available from Gibco/B R L, Bethesda, Md.; or AMV reverse transcriptase, available from Seikagaku America, Inc., St. Petersburg, Fla.). Synthetic oligonucleotide primers for PCR amplification can be designed. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a nucleic acid sequence of the present invention can be prepared by standard synthetic techniques, i.e., using an automated DNA synthesizer.

In another embodiment, the nucleic acid encodes a protein that is at least about 50%, preferably at least about 60%, more preferably at least about 70%, 75%, 80%, 85%, 90%, 91%, 92%, 93%, 94%, 95%, 96%, 97%, 98%, 99% or more homologous to a Gal1 epitope sequence described herein, or a fragment thereof.

It will be appreciated by those skilled in the art that DNA sequence polymorphisms that lead to changes in the amino acid sequences of a polypeptide can exist within a population (e.g., a mammalian and/or human population). Such genetic polymorphism in a gene can exist among individuals within a population due to natural allelic variation. As used herein, the terms "gene" and "recombinant gene" refer to nucleic acid molecules comprising an open reading frame encoding a polypeptide of the present invention, preferably a mammalian polypeptide. Such natural allelic variations can typically result in 1-5% variance in the nucleotide sequence of the gene. Any and all such nucleotide variations and resulting amino acid polymorphisms in a polypeptide that are the result of natural allelic variation and that do not alter the functional activity of the polypeptide are intended to be within the scope of the present invention. Nucleic acid molecules corresponding to natural allelic variants and homologues of interest can be isolated.

In addition to naturally-occurring allelic variants of a sequence that can exist in the population, the skilled artisan will further appreciate that changes can be introduced by mutation into the nucleotide sequence of a relevant Gal1 epitope nucleic acid sequence shown in Table 3 or orthologs thereof, thereby leading to changes in the amino acid sequence of the encoded protein, without altering the functional ability (e.g., neutralizing epitope) of the protein. For example, nucleotide substitutions leading to amino acid substitutions at "non-essential" amino acid residues can be made in the sequences. A "non-essential" amino acid residue is a residue that can be altered from the wild-type sequence without substantially altering the immunogenic properties or conformation, whereas an "essential" amino acid residue is one that affects the immunogenic properties or conformation. Other amino acid residues, however, (e.g., those that are not conserved or only semi-conserved between mouse and human) cannot be essential for activity and thus are likely to be amenable to alteration without altering polypeptide activity.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Gal1 neutralizing epitope, or ortholog or fragment thereof, can be created by introducing one or more nucleotide substitutions, additions or deletions into the nucleotide sequence of a template. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue is preferably replaced with another amino acid residue from the same side chain family. Alternatively, in another embodiment, mutations can be introduced randomly along all or part of a target coding sequence, such as by saturation mutagenesis, and the resultant mutants can be screened for a target polypeptide activity described herein to identify mutants that retain polypeptide activity. Following mutagenesis, the encoded protein can be expressed recombinantly (as described herein) and the activity of the protein can be determined using, for example, assays described herein.

Levels of proteins of interest (e.g., Gal1 neutralizing epitope containing peptides or target Gal1 polypeptides) can be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In some embodiments, such protein expression levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In other embodiments, mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays.

As an alternative to making determinations based on the absolute expression level, determinations can be based on the normalized expression level. Expression levels are normalized by correcting the absolute expression level by comparing its expression to the expression of a non-target gene, e.g., a housekeeping or other reference gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a polypeptide can also be detected and/or quantified by detecting or quantifying the expressed polypeptide. The desired polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the polypeptide of interest.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the present invention relates to a vector comprising a nucleic acid of the present invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv-positive cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

The nucleic acids of the present invention may be used to produce a recombinant polypeptide of the present invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL 1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the present invention according to the invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the present invention. A cell culture includes host cells, media and other byproducts. Suitable media for cell culture are well known in the art. A polypeptide of interest or fragment thereof, can be secreted and isolated from a mixture of cells and medium containing the polypeptide. Alternatively, a polypeptide or fragment thereof, can be retained cytoplasmically and the cells harvested, lysed and the protein or protein complex isolated. A polypeptide of interest or fragment thereof, can be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of a polypeptide of interest or a fragment thereof. In other embodiments, heterologous tags can be used for purification purposes (e.g., epitope tags and FC fusion tags), according to standards methods known in the art.

In another aspect, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences. Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra; each entirely incorporated herein by reference.

IV. Methods of Producing Polypeptides and Antibodies

Polypeptides and antibodies and fragments thereof, immunoglobulins, and polypeptides of the present invention may be produced by any technique known in the art or described herein, such as, without limitation, any chemical, biological, genetic or enzymatic technique, either alone or in combination.

For example, host cells can be cultured to express a polypeptide or antibody of interest. A cell culture includes host cells, media and other byproducts. Suitable media for cell culture are well known in the art. A polypeptide of interest or fragment thereof, can be secreted and isolated from a mixture of cells and medium containing the polypeptide. Alternatively, a polypeptide of interest or fragment thereof, can be retained cytoplasmically and the cells harvested, lysed and the protein or protein complex isolated. A polypeptide of interest or fragment thereof, can be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of a polypeptide of interest or a fragment thereof. In other embodiments, heterologous tags can be used for purification purposes (e.g., epitope tags and FC fusion tags), according to standards methods known in the art.

Thus, a nucleotide sequence encoding all or a selected portion of a polypeptide of interest can be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, can be employed to prepare recombinant polypeptides of interest or fragments thereof, by microbial means or tissue-culture technology in accord with the subject invention.

In another variation, protein production can be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system can be used. Such systems typically comprise at least an RNA polymerase holoenzyme, ribonucleotides and any necessary transcription initiation, elongation and termination factors. In vitro transcription and translation can be coupled in a one-pot reaction to produce proteins from one or more isolated DNAs.

In certain embodiments, a polypeptide of interest or fragment thereof, can be synthesized chemically, ribosomally in a cell free system, or ribosomally within a cell. Chemical synthesis can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full-length ligation products are chemically identical to proteins produced by cell free synthesis. Full length ligation products can be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T.

K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

In particular, the present invention further relates to a method of producing an antibody or a polypeptide of the present invention, which method comprises the steps consisting of: (i) culturing a transformed host cell according to the invention under conditions suitable to allow expression of said antibody or polypeptide; and (ii) recovering the expressed antibody or polypeptide.

Antibodies and other polypeptides of the present invention are suitably separated from the culture medium by conventional immunoglobulin purification procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Chimeric antibodies (e.g., mouse-human chimeras) of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. The CH domain of a human chimeric antibody can be any region which belongs to human immunoglobulin, such as the IgG class or a subclass thereof, such as IgG1, IgG2, IgG3 and IgG4. Similarly, the CL of a human chimeric antibody can be any region which belongs to Ig, such as the kappa class or lambda class. chimeric and humanized monoclonal antibodies, comprising both human and non-human portions, which can be made using standard recombinant DNA techniques, are within the scope of the present invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125, 023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225, 539; Jones et al. (1986) Nature 321:552-525; Verhoeyan et al. (1988) Science 239:1534; and Beidler et al. (1988) J. Immunol. 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. Humanized antibodies of the present invention can be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type).

Methods for producing humanized antibodies based on conventional recombinant DNA and gene transfection techniques are well known in the art (See, e.g., Riechmann L et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Similarly, bispecific or multispecific antibodies described herein can be made according to standard procedures. For example, triomas and hybrid hybridomas are two examples of cell lines that can secrete bispecific or multispecific antibodies. Examples of bispecific and multispecific antibodies produced by a hybrid hybridoma or a trioma are disclosed in U.S. Pat. No. 4,474,893. Such antibodies can also be constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Alternatively, such antibodiescan also be generated by making heterohybridomas by fusing hybridomas or other cells making different antibodies, followed by identification of clones producing and co-assembling the desired antibodies. They can also be generated by chemical or genetic conjugation of complete immunoglobulin chains or portions thereof such as Fab and Fv sequences. The antibody component can bind to a polypeptide or a fragment thereof of one or more biomarkers of the present invention, including one or more immunoinhibitory biomarkers described herein.

In addition, methods for producing antibody fragments are well known. For example, Fab fragments of the present invention can be obtained by treating an antibody which specifically reacts with human GAL1 with a protease, papaine. Also, Fabs can be produced by inserting DNA encoding Fabs of the antibody into a vector for prokaryotic expression system, or for eukaryotic expression system, and introducing the vector into a procaryote or eucaryote (as appropriate) to express the Fabs.

Similarly, F(ab')2 fragments of the present invention can be obtained treating an antibody which specifically reacts with GAL1 with a protease, pepsin. Also, the F(ab')2 fragment can be produced by binding Fab' described below via a thioether bond or a disulfide bond.

Fab' fragments of the present invention can be obtained treating F(ab')2 which specifically reacts with hGAL1 with a reducing agent, dithiothreitol. Also, the Fab' fragments can be produced by inserting DNA encoding a Fab' fragment of the antibody into an expression vector for prokaryote, or an expression vector for eukaryote, and introducing the vector into a prokaryote or eukaryote (as appropriate) to perform its expression.

In addition, scFvs of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

V. Modification of Polypeptides and Antibodies

Amino acid sequence modification(s) of the polypeptides and antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the polypeptide or antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the present invention, or corresponding DNA sequences which encode said polypeptides, without appreciable loss of their biological activity.

In one embodiment, amino acid changes may be achieved by changing codons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the polypeptide or antibody of the present invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Other modifications can involve the formation of immunoconjugates. For example, in one type of covalent modification, antibodies or proteins are covalently linked to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features anti-Gal1 antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-Gal1 antibodies can be used therapeutically in tissue as part of a treatment regimen. In some embodiments, detection is useful and detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

VI. Uses and Methods of the Present Invention

The anti-Gal1 neutralizing epitope agents described herein (e.g., nucleic acids, polypeptides, vectors, host cells, and the like) can be used to design anti-Gal1 neutralizing agents. In particular, information useful for the design of anti-Gal1 therapeutic agents, including, for example, the protein domain, structural information, and the like for polypeptides of the present invention is described herein.

a. Screening Assays

In certain exemplary embodiments, screening assays for identifying modulators, i.e., candidate or test compounds or agents (e.g., antibodies, peptides, cyclic peptides, peptidomimetics, small molecules, small organic molecules, or other drugs) which have an inhibitory effect on Gal1 activity are provided.

Such modulators be identified and developed as described herein using techniques and methods known to those of skill in the art. The modulators of the present invention can be used to inhibit Gal1 activity and/or to prevent or treat Gal1-mediated disorders. A number of methods for identifying such modulators are known in the art. For example, in one such method, a Gal1 nucleic acid or polypeptide is contacted with a test agent and Gal1-mediated glycan binding activity is determined in the presence of the test compound, wherein a decrease in the activity in the presence of the compound as compared to the activity in the absence of the compound (or in the presence of a control compound) indicates that the test agent modulates (e.g., inhibits or neutralizes) the activity of Gal1.

Agents to be tested for their ability to act as modulators (e.g., inhibits or neutralizers) of Gal1 activity, can be produced, for example, by bacteria, yeast or other organisms (e.g. natural products), produced chemically (e.g. small molecules, including peptidomimetics), or produced recombinantly. Compounds for use with the above-described methods can be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide.

A variety of assay formats will suffice and, in light of the present disclosure, those not expressly described herein can nevertheless be comprehended by one of ordinary skill in the art based on the teachings herein. Assay formats can be generated in many different forms and include assays based on cell-free systems, e.g. purified proteins or cell lysates, as well as cell-based assays which utilize intact cells. Simple binding assays can also be used to detect agents which modulate Gal1 activity, for example, by inhibiting the formation of a Gal1-glycan complex or interaction. Another example of an assay useful for identifying an inhibitor of Gal1 activity is a competitive assay that combines one or more Gal1 polypeptides with a potential modulator, such as, for example, polypeptides, nucleic acids, natural substrates or ligands, antibodies, or substrate or ligand mimetics, under appropriate conditions for a competitive inhibition assay. Assays can employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

Interaction between Gal1 and a substrate, such as lactoasamine sequences (Galβ1,4 GlcNAc or poly-LacNAc residues on N-glycans and/or O-glycans, such as complex N-glycans or core 2 O-glycans) can be detected by a variety of methods. Modulation of the complex's formation can be quantified using, for example, detectably labeled proteins such as radiolabeled, fluorescently labeled, or enzymatically labeled polypeptides or binding partners, by immunoassay, or by chromatographic detection.

In certain embodiments, it can be desirable to immobilize a test reagent to facilitate separation of desired reactants or products, as well as to accommodate automation of the assay. For example, polypeptides of the present invention can be bonded to a carrier molecule or immobilized on an object. In one embodiment, the object is selected from the group consisting of a cell, a metal, a resin, a polymer, a ceramic, a glass, a microelectrode, a graphitic particle, a bead, a gel, a plate, an array, and a capillary tube. Assays can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/polypeptide (GST/polypeptide) fusion proteins can be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions can be desired. Following incubation, the beads are washed to remove any unbound label, and the matrix immobilized and radiolabel determined directly (e.g., beads placed in scintillant), or in the supernatant after the complexes are subsequently dissociated. Alternatively, the complexes can be dissociated from the matrix, separated by SDS-PAGE, and the level of target polypeptides found in the bead fraction quantified from the gel using standard electrophoretic techniques such as described in the appended examples.

Other techniques for immobilizing proteins on matrices are also available for use in the subject assay. For instance, a protein can be immobilized utilizing conjugation of biotin and streptavidin. For instance, biotinylated polypeptide molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, anti-Gal1 neutralizing antibodies reactive with a polypeptide described herein can be derivatized to the wells of the plate, and polypeptide trapped in the wells by antibody conjugation. As above, preparations of a binding partner and a test compound are incubated in the polypeptide presenting wells of the plate, and the amount of complex trapped in the well can be quantified. Exemplary methods for detecting such complexes, in addition to those described above for the GST-immobilized complexes, include immunodetection of complexes using antibodies reactive with the binding partner, or which are reactive with the polypeptide and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the binding partner.

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system can be derived to favor discovery of modulators of particular intermediate states of the protein-protein interaction. For instance, a reconstituted protein assay can be carried out both in the presence and absence of a candidate agent, thereby allowing detection of a modulator of a given protein-substrate, protein-protein, or nucleic acid-protein interaction.

In still further embodiments, the Gal1 agent expressing a neutralizing Gal1 epitope can be generated in whole cells, taking advantage of cell culture techniques to support the subject assay. For example, the agent can be constituted in a prokaryotic or eukaryotic cell culture system. This allows for an environment more closely approximating that which therapeutic use of the modulator would require, including the ability of the agent to gain entry into or contact a cell. Furthermore, certain of the in vivo embodiments of the assay are amenable to high through-put analysis of candidate agents.

Some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker.

The amount of transcription from the reporter gene can be measured using any method known to those of skill in the art to be suitable. For example, specific mRNA expression can be detected using Northern blots or specific protein product can be identified by a characteristic stain, Western blots or an intrinsic activity. In certain embodiments, the product of the reporter gene is detected by an intrinsic activity associated with that product. For instance, the reporter gene can encode a gene product that, by enzymatic activity, gives rise to a detection signal based on color, fluorescence, or luminescence.

In many drug screening programs which test libraries of compounds (e.g., phage display) and natural extracts, high throughput assays are desirable in order to maximize the number of compounds surveyed in a given period of time. Assays of the present invention which are performed in cell-free systems, such as can be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as can be manifest in an alteration of binding affinity with other proteins or changes in enzymatic properties of the molecular target.

Gal1 activity can be identified and/or assayed using a variety of methods well known to the skilled artisan as described above. For example, targeted disruption of Gal1-glycan interactions, through Gal1 blockade or prevention of N-glycan branching, can be assayed. Such assays are well known in the art (see, for example, U.S. Pat. Publ. 2013/0011409 and PCT Pat. Publ. WO 2011/060272).

b. Methods of Using Immunogens

As described above, the present invention provides compositions useful as immunogens (e.g., polypeptides, nucleic acids, vectors, host cells, immunogenic compositions, and the like described herein). Such immunogens can be administered in any of a number of routes known in the art (e.g., to be compatible with eliciting strong antibody responses). Administration can be by injection, infusion, aerosol, oral, transdermal, transmucosal, intrapleural, intrathecal, or other suitable routes. Preferably, the composition is administered by intravenous, subcutaneous, intradermal, or intramuscular routes, or any combination thereof. The immunization protocol can include at least one priming dose, followed by one or multiple boosting doses administered over time. An exemplary range for an immunogenically effective amount of the present immunogenic polypeptides is about 5 to about 500 µg/kg body weight. A preferred range is about 10-100 µg/kg.

In one embodiment, one or more unit doses of the immunogen are given at one, two or three time points. The optimal number and timing of boosts can readily be determined using routine experimentation. Exemplary "prime-boost" regimens are described in U.S. Pat. No. 6,210,663 and WO 00/44410. One method according to the present invention involves "priming" a mammalian subject by administration of a priming composition. "Priming," as used herein, means any method whereby a first immunization using an antigen permits the generation of an immune response to the antigen upon a second immunization with the same antigen, wherein the second immune response is greater than that achieved where the first immunization is not provided.

Preferably, a boosting composition is administered about 2 to 27 weeks after administering the priming composition to a mammalian subject. The administration of the boosting composition is accomplished using an effective amount of a boosting composition containing or capable of delivering the same antigen as administered by the priming composition. As used herein, the term "boosting composition" includes, as one embodiment, a composition containing the same antigen as in the priming composition or precursor thereof, but in a different form, in which the boosting composition induces an immune response in the host. In one particular embodiment, the boosting composition comprises a recombinant soluble protein.

In one embodiment, a boosting composition is a replication-competent or replication-defective recombinant virus containing the DNA sequence encoding the protein antigen. An example of a boosting composition is a bacterial recombinant vector containing the DNA sequence encoding the antigen in operable association with regulatory sequences directing expression of the antigen in tissues of the mammal. One example is a recombinant BCG vector. Other examples include recombinant bacterial vectors based on Salmonella, Shigella, and Listeria, among others. Still another example of a boosting composition is a naked DNA sequence encoding the antigen in operable association with regulatory sequences directing expression of the antigen in tissues of the mammal but containing no additional vector sequences. These vaccines can further contain pharmaceutically suitable or physiologically acceptable carriers. In still additional embodiments, the boosting compositions can include proteins or peptides (intact and denatured), heat-killed recombinant vaccines, inactivated whole microorganisms, antigen-presenting cells pulsed with the instant proteins or infected/transfected with a nucleic acid molecule encoding same, and the like, all with or without adjuvants, chemokines and/or cytokines.

Representative forms of antigenic immunogens include a "naked" DNA plasmid, a "naked" RNA molecule, a DNA molecule packaged into a replicating or nonreplicating viral vector, an RNA molecule packaged into a replicating or nonreplicating viral vector, a DNA molecule packaged into a bacterial vector, or proteinaceous forms of the antigen alone or present in virus-like particles, or combinations thereof.

In one embodiment, immunogenic agents of interest can be administered to subjects. In some embodiments, fusion proteins can be constructed and administered which have enhanced biological properties. In addition, the polypeptides can be modified according to well-known pharmacological methods in the art (e.g., pegylation, glycosylation, oligomerization, etc.) in order to further enhance desirable biological activities, such as increased immunogenicity, bioavailability, and/or decreased proteolytic degradation.

In one embodiment, "virus-like particles" or "VLPs" can be used, which are non-infectious particles in any host and do not contain all of the protein components of live virus particles. In one embodiment, VLPs contain the polypeptides described herein and form membrane-enveloped virus-like particles. The advantages of using VLPs include (1) their particulate and multivalent nature, which is immunostimulatory, and (2) their ability to present the disulfide-stabilized envelope glycoproteins in a near-native, membrane-associated form. VLPs are produced by co-expressing the viral proteins (e.g., polypeptides described herein) in the same cell. This can be achieved by any of several means of heterologous gene expression that are well-known to those skilled in the art, such as transfection of appropriate expression vector(s) encoding the viral proteins, infection of cells with one or more recombinant viruses (e.g., vaccinia) that encode the VLP proteins, or retroviral transduction of the cells. A combination of such approaches can also be used. The VLPs can be produced either in vitro or in vivo. VLPs can be produced in purified form by methods that are well-known to the skilled artisan, including centrifugation, as on sucrose or other layering substance, and by chromatography.

For embodiments using instant nucleic acid delivery, any means for the introduction of a polynucleotide into a subject, such as a human or non-human mammal, or cells thereof can be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs can first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, can then be effected using known methods and materials and delivered to the recipient mammal. See, e.g., Canonico et al., Am J Respir Cell Mol Biol 10:24-29, 1994; Tsan et al., Am J Physiol 268; Alton et al., Nat Genet. 5:135-142, 1993; and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest can be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter can be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences, such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued Can 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxvirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

Immunogens can be administered together with an adjuvant or other immunostimulant. Thus, the immunogens can further comprise one or more adjuvants or immunostimulating agents, which are preferably added to the fusion protein immunogens using for boosting the immune response. An adjuvant is any substance that can be added to an immunogen or to a vaccine formulation to enhance the immune-stimulating properties of the immunogenic moiety, such as a protein or polypeptide. Liposomes are also considered to be adjuvants. See, for example, Gregoriades, G. et al., Immunological Adjuvants and Vaccines, Plenum Press, New York, 1989; Michalek, S. M. et al., Liposomes as Oral Adjuvants, Curr. Top. Microbiol. Immunol. 146:51-58 (1989). Examples of adjuvants or agents that can add to the effectiveness of immunogens include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g., N-acetyl-D-glucosaminyl-(β,1-4)-N-acetylmuramyl-L-alanyl-D-isoglutami-ne (GMDP) (Hornung, R L et al., Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al., (1992) N. Engl. J. Med., 327: 1209-1238) and monophosphoryl lipid A adjuvant solubilized in 0.02% triethanolamine Other useful adjuvants are, or are based on, bacterial endotoxin, lipid X, whole organisms or subcellular fractions of the bacteria Propionobacterium acnes or Bordetella pertussis, polyribonucleotides, sodium alginate, lanolin, lysolecithin, vitamin A, saponin and saponin derivatives such as QS21 (White, A. C. et al. (1991) Adv. Exp. Med. Biol., 303:207-210) which is now in use in the clinic (Helling, F et al. (1995) Cancer Res., 55:2783-2788; Davis, T A et al. (1997) Blood, 90: 509A (abstr.)), levamisole, DEAE-dextran, blocked copolymers or other synthetic adjuvants. Examples of commercially available adjuvants include (a) Amphigen®, which is an oil-in-water adjuvant made of de-oiled lecithin dissolved in oil (see for example, U.S. Pat. No. 5,084,269 and US Pat Publication 20050058667A1 and (b) Alhydrogel®, which is an aluminum hydroxide gel. Aluminum is approved for human use. Adjuvants are available commercially from various sources, for example, Merck Adjuvant 65® (Merck and Company, Inc., Rahway, N.J.). The immunogenic material can be adsorbed to or conjugated to beads such as latex or gold beads, ISCOMs, and the like. There is evidence that traditional formulations, such as Freund's adjuvant (both complete and incomplete) and Alum gel at least partially denature antigen resulting in the destruction or under-representation of conformational epitopes. The Ribi adjuvant system (RAS), which belongs to the monophos-phoryl-lipid A (MPL) containing-adjuvants, can be used to overcome this problem. Results from several studies indicate that antigen formulated using MPL-containing adjuvants elicited antibodies that preferentially bound native rather than denatured antigen (Earl, P. L., et al., J. Virol 68:3015-3026 (1994); VanCott T. C., et al., J. Virol 71:4319-4330 (1997)).

Immunogens can also be supplemented with an immunostimulatory cytokine, lymphokine or chemokine. Exemplary cytokines include, without limitation, GM-CSF (granulocyte-macrophage colony stimulating factor), interleukin 1, interleukin 2, interleukin 12, interleukin 18 or interferon-gamma.

General methods to prepare immunogenic pharmaceutical compositions and vaccines are well known in the art (see, for example, Remington's Pharmaceutical Science; Mack Publishing Company Easton, Pa.).

In one aspect, the present invention provides immunogens that can be used to raise anti-Gal1 neutralizing agents (e.g., antibodies and aptamers) by methods known to those of ordinary skill in the art. The antibodies raised can then be administered to a subject having a Gal1-mediated disorder or to prevent a Gal1-mediated disorder. In one embodiment involving hybridoma production, samples can be screened by a number of techniques to characterize binding to immunogens described herein. One approach involves ELISA binding to the inventive immunogens. Animals with sera samples which test positive for binding to one or more immunogens are candidates for use in MAb production. The criteria for selection of animals to be used in MAb production is based on the evidence of neutralizing antibody in the animals' sera or, in the absence of neutralization, appropriate binding patterns against the desired immunogens.

Hybridoma supernatants derived from MAb production can be screened for ELISA, lysate and surface immunopre-cipitation assays for binding to the desired immunogen. Samples which are positive in any of the binding assays can be screened to confirm their ability to neutralize Gal1 activity as described above. For any assay described herein, results from test agents can be compared against titration or positive controls (e.g., known broadly neutralizing antibodies) for normalization purposes.

c. Therapeutic Methods

In one aspect, the present invention provides a method of preventing a subject from becoming afflicted with a Gal1-mediated disorder comprising administering to the subject a prophylactically effective amount of a Gal1 neutralizing agent described herein to thereby prevent the subject from becoming afflicted with the Gal1-mediated disorder.

In another aspect, the present invention provides a method for reducing the likelihood of a subject's becoming infected with a Gal1-mediated disorder comprising administering to the subject a prophylactically effective amount of a Gal1 neutralizing agent described herein to thereby reducing the likelihood of the subject's becoming afflicted with the Gal1-mediated disorder.

In still another aspect, the present invention provides a method for preventing or delaying the onset of, or slowing the rate of progression of, a Gal1-mediated disorder in a subject, comprising administering to the subject a therapeutically effective amount of a Gal1 neutralizing agent described herein to thereby prevent or delay the onset of, or slowing the rate of progression of, the Gal1-mediated disorder in the subject.

Thus, in some embodiments, the immunogens described herein can be used to immunize a subject such that unwanted Gal1 activity will be reduced in the subject. In other embodiments, the immunogens described herein can be employed to immunize a subject not afflicted with a Gal1-mediated disorder.

It will be appreciated that individual dosages can be varied depending upon the requirements of the subject in the judgment of the attending clinician, the severity of the condition being treated and the particular compound being employed. In determining the therapeutically effective amount or dose, a number of additional factors can be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bio-availability characteristics of the preparation administered; the dose regimen selected; the kind of concurrent treatment; and other relevant circumstances.

The therapeutic dose can be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like. Treatment can be initiated with smaller dosages which are less than the effective dose of the compound. Thereafter, in one embodiment, the dosage should be increased by small increments until the optimum effect under the circumstances is reached. For convenience, the total daily dosage can be divided and administered in portions during the day if desired.

The duration and/or dose of treatment with antiviral therapies can vary according to the particular agent or combination thereof. An appropriate treatment time for a particular antiviral therapeutic agent will be appreciated by the skilled artisan. The invention contemplates the continued assessment of optimal treatment schedules for each antiviral therapeutic agent, where the phenotype of the Gal1-mediated disorder of the subject as determined by the methods of the invention is a factor in determining optimal treatment doses and schedules.

The compositions described herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the compositions can be suitably administered by pulse infusion, particularly with declining doses of the antibody.

In general, it is preferable to obtain a first sample from the subject prior to beginning therapy and one or more samples during treatment. In such a use, a baseline of expression of cells from subjects with a Gal1-mediated disorder prior to therapy is determined and then changes in the baseline state of expression of cells from subjects with the Gal1-mediated disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with a Gal1-mediated disorder is increasing or decreasing.

It may further be advantageous to administer the immunogenic compositions disclosed herein with other agents, such as proteins, peptides, antibodies, and other anti-Gal1 agents. For example, therapeutic synergies are believed to become manifested when treating a cell expressing Gal1 and another immunoinhibitory molecule, such as PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof. In certain embodiments, the immunonogenic compositions are administered sequentially with other therapeutic agents, such as before or after the other agent. One of ordinary skill in the art would know that sequential administration can mean immediately following or after an appropriate period of time, such as hours days, weeks, months, or even years later.

In certain embodiments, the treatment is of a mammal, such as a human

In another aspect, the present invention provides pharmaceutically acceptable compositions which comprise a therapeutically-effective amount of a composition described herein, formulated together with one or more pharmaceutically acceptable carriers (additives) and/or diluents and with or without additional antiviral agents and/or immunogens. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., neutralizes) Gal1 expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., neutralizes) Gal1 expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., neutralizes) Gal1 expression and/or activity, with the carrier and, optionally, one or more accessory ingredients. In general, the formulations are prepared by uniformly and intimately bringing into association an agent with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. A compound can also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered peptide or peptidomimetic moistened with an inert liquid diluent.

Tablets, and other solid dosage forms, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration can be presented as a suppository, which can be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., neutralizes) Gal1 expression and/or activity include powders, sprays, ointments, pastes, creams, lotions, gels, solutions, patches and inhalants. The active component can be mixed under sterile conditions with a pharmaceutically-acceptable carrier, and with any preservatives, buffers, or propellants which can be required.

The ointments, pastes, creams and gels can contain, in addition to an agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., neutralizes) Gal1 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., neutralizes) Gal1 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., neutralizes) Gal1 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

Actual dosage levels of the active ingredients in the pharmaceutical compositions of this invention can be determined by the methods of the present invention so as to obtain an amount of the active ingredient, which is effective to achieve the desired therapeutic response for a particular subject, composition, and mode of administration, without being toxic to the subject.

Nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VII. Kits

In addition, the present invention also encompasses kits comprising anti-Gal1 agents described herein. For example, the kit can comprise a neutralizing anti-Gal1 antibody with or without additional therapeutic agents, such as an immune checkpoint inhibitor. The agent can be packaged in a suitable container. For example, the present invention provides kits comprising at least one immunogenic peptide and/or one antibody described herein. Kits of the present invention can contain an immunogenic peptide and/or antibody coupled to a solid support, e.g., a tissue culture plate or beads (e.g., sepharose beads).

A kit can include additional components to facilitate the particular application for which the kit is designed. Exemplary agents that kits can contain include reagents necessary for controls (e.g., control biological samples or Gal1 protein standards). A kit may additionally include buffers and other reagents recognized for use in a method of the disclosed invention. Non-limiting examples include agents to reduce non-specific binding, such as a carrier protein or a detergent. A kit of the present invention can also include instructional materials disclosing or describing the use of the kit or an antibody of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Figure 2:
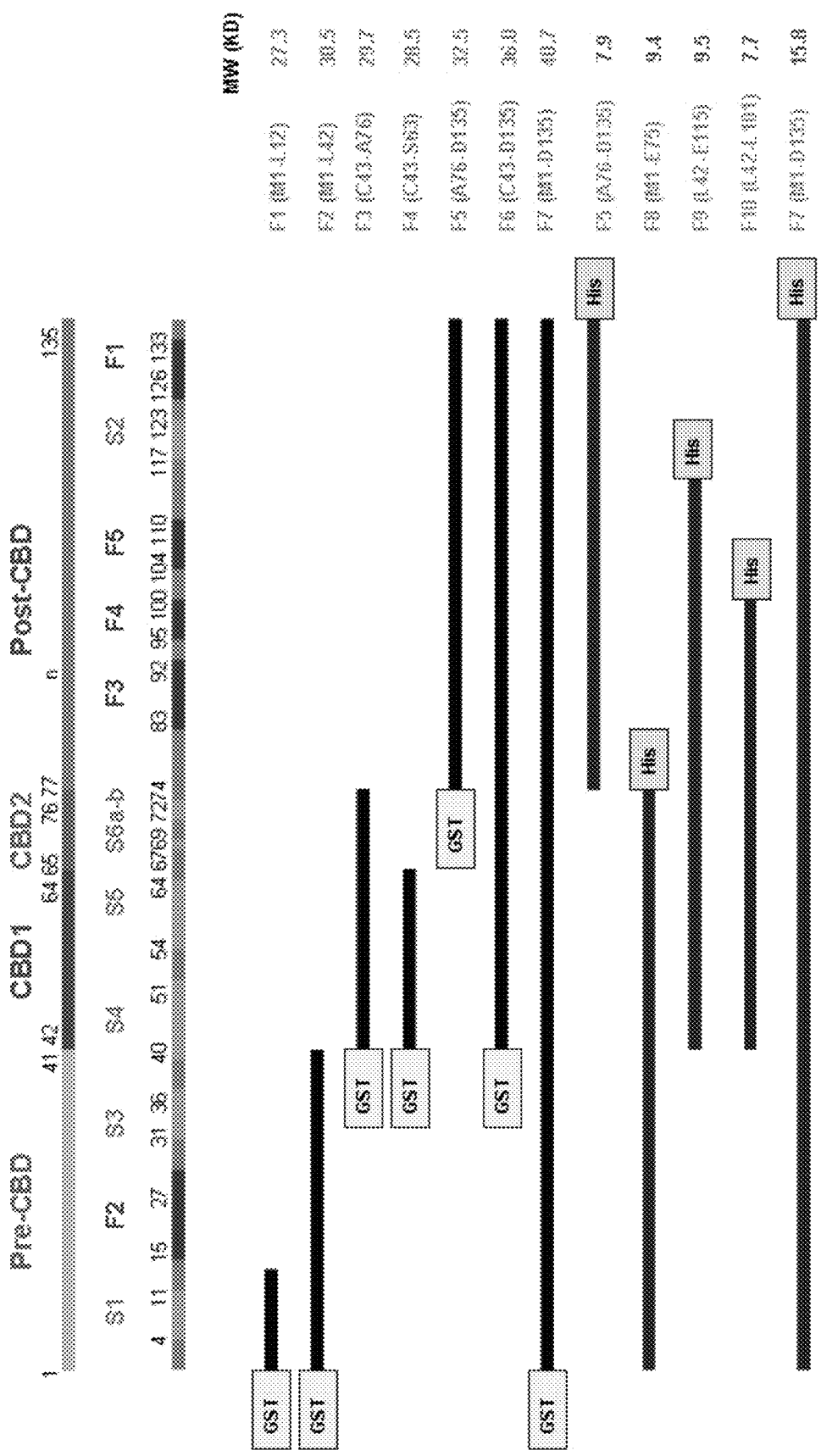
FIG. 2 shows a schematic diagram of recombinant GST-tagged or HIS-tagged human Gal1 (hGal1) and fragments.

Example 1: Neutralizing Anti-Gal1 Monoclonal Antibodies Useful for Therapeutic Applications Neutralizing anti-Gal1 monoclonal antibodies were generated and reacted with human recombinant Gal1 and endogenous Gal1 in biochemical assays and in immunohistochemical analyses of primary tumors. In addition, several of the Gal1 monoclonal antibodies also cross-reacted well with endogenous Gal1 from cynomologous monkey and mouse (FIG. 1). Epitope mapping indicated that the 8B5, 8F4 and 8G3 Gal1 monoclonal antibodies all recognized a domain distal to the previously described carbohydrate-binding domain (FIG. 2 and Table 1).

These antibodies (i.e., 8B5, 8F4, and 8G3) were subsequently sequenced and determined to each have the same sequence, with the light chain being lambda. Briefly, total RNA was extracted from each hybridoma and subjected to RT-PCR using constant region specific 3' primers and pools of degenerate signal sequence specific 5' primers. Amplified products were cloned and sequenced. For the heavy chain, a total of 36 clones were sequenced; and for the light chain, a total of 19 clones were sequenced. Sequence alignments yielded the same heavy and light chain sequences for all clones across all three antibodies. These sequences are presented in Table 1 below and analysis of the sequences obtained from the hybridomas is summarized in Table 2 below. In addition, hybridoma cell line 8F4.F8.G7 was deposited with the American Type Culture Collection and was received on Dec. 17, 2009 in accordance with the provisions of the Budapest Treaty on the International Recognition of the Deposit of Microorganisms for the Purposes of Patent Procedure under deposit number PTA-10535. U.S. Pat. Publ. 2013/0011409 and PCT Pat. Publ. WO 2011/060272 disclose the 8F4 antibody and are each incorporated herein in their entirety by this reference.

TABLE 1

Epitope mapping and sequences of anti-human Gal1 monoclonal antibodies

| mAbs | Mapping | Domain recognition |
|---|---|---|
| 8B5.E6.2H3 | GST-F5; GST-F6; GST-F7 | Post-CBD |
| 8B5.E6.H9 | GST-F5; GST-F6; GST-F7 | Post-CBD |
| 8F4.F8.G7 | GST-F5; GST-F6; GST-F7 | Post-CBD |
| 8F4.F8.H2 | GST-F5; GST-F6; GST-F7 | Post-CBD |
| 8G3.B1.G12 | GST-F5; GST-F6; GST-F7 | Post-CBD |
| 8G3.B1.H8 | GST-F5; GST-F6; GST-F7 | Post-CBD |
| 2E5.2H12 | GST-F3; GST-F6; GST-F7 | CBD2 |

8B5, 8F4, and 8G3 Heavy Chain Variable (vH) DNA and Amino Acid Sequences*

```
         10         20         30         40         50         60         70         80         90        100
GAGGTTCAGCTGCAGCAGTCTGTGGCAGAGTTTGTGAGGCCAGGGGCCTCAGTCAGGTTGTCCTGCACAGCTTCTGGCTTCAACATTAAAAACACCTATA
   E  V  Q  L  Q  Q  S  V  A  E  F  V  R  P  G  A  S  V  R  L  S  C  T  A  S  G  F  N  I  K  N  T  Y 110        120        130        140        150        160        170        180        190        200
TACACTGGGTGAGGCAGAGGCCTGAACAGGGCCTGGAGTGGATTGGAAAGATTGATCCTGCGAATGGTAATACTAAATATGTCCCGGAGTTCCAGGGCAA
   I  H  W  V  R  Q  R  P  E  Q  G  L  E  W  I  G  K  I  D  P  A  N  G  N  T  K  Y  V  P  E  F  Q  G  K 210        220        230        240        250        260        270        280        290        300
GGCCACTATGACTGCGGACACATCCTCCAACACAGTCTACCTGCACCTCAGCAGCCTGACATCTGAGGACACTGCCATCTATTACTGTGTCGATGGTTAC
   A  T  M  T  A  D  T  S  S  N  T  V  Y  L  H  L  S  S  L  T  S  E  D  T  A  I  Y  Y  C  V  D  G  Y
```

TABLE 1-continued

Epitope mapping and sequences of anti-human Gal1 monoclonal antibodies

```
           310       320       330       340       350
TACGGCTGGTATTTCGCTGTCTGGGGCACAGGGACCCACGGTCACCGTCTCCTCA
 Y  G  W  Y  F  A  V  W  G  T  G  T  T  V  T  V  S  S

8B5, 8F4, and 8G3 including 8F4F8G7, Light Chain Variable (vL) DNA and Amino Acid Sequences*
      10        20        30        40        50        60        70        80        90       100
CAGGCTGTTGTGACTCAGGAATCTGCACTCACCACATCACCTGGTGAAACAGTCACACTCACTTGTCGCTCAAGCACTGGGGCTGTTACAACTAGTAACT
 Q  A  V  V  T  Q  E  S  A  L  T  T  S  P  G  E  T  V  T  L  T  C  R  S  S  T  G  A  V  T  T  S  N 110       120       130       140       150       160       170       180       190       200
ATGCCAACTGGGTCCAAGAAAAACCAGATCATTTATTCACTGGTCTAATAGGTGCTACCAACAACCGAGCTCCAGGTGTTCCTGCCAGATTCTCAGGCTC
 Y  A  N  W  V  Q  E  K  P  D  H  L  F  T  G  L  I  G  A  T  N  N  R  A  P  G  V  P  A  R  K  S  G  S 210       220       230       240       250       260       270       280       290       300
CCTGATTGGAGACAAGGCTGTCCTCACCATCACAGGGGCACAAACTGAGGATGAGGCAATATATTTCTGTGCTCTATGGTACAGAAACCATTTTATTTTC
  L  I  G  D  K  A  V  L  T  I  T  G  A  Q  T  E  D  E  A  I  Y  F  C  A  L  W  Y  R  N  H  F  I  F 310       320
GGCAGTGGAACCAAGGTCACTGTCCTC
  G  S  G  T  K  V  T  V  L 8B5, 8F4, and 8G3, including 8F4F8G7, Heavy Chain Variable (vH) DNA Sequence*
GAGGTTCAGCTGCAGCAGTCTGTGGCAGAGTTTGTGAGGCCAGGGGCCTCAGT
CAGGTTGTCCTGCACAGCTTCTGGCTTCAACATTAAAAACACCTATATACACTG
GGTGAGGCAGAGGCCTGAACAGGGCCTGGAGTGGATTGGAAAGATTGATCCTG
CGAATGGTAATACTAAATATGTCCCGGAGTTCCAGGGCAAGGCCACTATGACT
GCGGACACATCCTCCAACACAGTCTACCTGCACCTCAGCAGCCTGACATCTGAG
GACACTGCCATCTATTACTGTGTCGATGGTTACTACGGCTGGTATTTCGCTGTCT
GGGGCACAGGGACCACGGTCACCGTCTCCTCA 8B5, 8F4, and 8G3, including 8F4F8G7, Light Chain Variable (vK) DNA Sequence*
CAGGCTGTTGTGACTCAGGAATCTGCACTCACCACATCACCTGGTGAAACAGTC
ACACTCACTTGTCGCTCAAGCACTGGGGCTGTTACAACTAGTAACTATGCCAAC
TGGGTCCAAGAAAAACCAGATCATTTATTCACTGGTCTAATAGGTGCTACCAAC
AACCGAGCTCCAGGTGTTCCTGCCAGATTCTCAGGCTCCCTGATTGGAGACAAG
GCTGTCCTCACCATCACAGGGGCACAAACTGAGGATGAGGCAATATATTTCTGT
GCTCTATGGTACAGAAACCATTTTATTTTCGGCAGTGGAACCAAGGTCACTGTC
CTC 8B5, 8F4, and 8G3, including 8F4F8G7, Heavy Chain Variable (vH) Amino Acid Sequence*
EVQLQQSVAEFVRPGASVRLSCTASGFNIKNTYIHWVRQRPEQGLEWIGKIDPANG
NTKYVPEFQGKATMTADTSSNTVYLHLSSLTSEDTAIYYCVDGYYGWYFAVWGT
GTTVTVSS 8B5, 8F4, and 8G3, including 8F4F8G7, Light Chain Variable (vK) Amino Acid Sequence*
QAVVTQESALTTSPGETVTLTCRSSTGAVTTSNYANWVQEKPDHLFTGLIGATNNR
APGVPARFSGSLIGDKAVLTITGAQTEDEAIYFCALWYRNHFIFGSGTKVTVL
```

*CDR definitions and protein sequence numbering according to Kabat. CDR nucleotide and protein sequences are highlighted in red color or underlining in order of CDR1, CDR2, and CDR3, respectively.

TABLE 2

Summary of sequences of anti-human Gal1 monoclonal antibodies
Antibody Sequence Analysis[a]

|  | H Chain | L Chain |
|---|---|---|
| CDR 1 Length | 5 aa | 14 aa |
| CDR 2 Length | 17 aa | 7 aa |
| CDR 3 Length | 9 aa | 9 aa |
| Closest Human Germline[b] | IGHV1-46 (62%) | IGLV7-46 (62%) |
| Closest Human FW1[b] | IGHV3-49 (67%) | IGLV7-46 (82%) |
| Closest Human FW2[b] | IGHV1-46 (79%) | IGLV7-43 (42%) |
| Closest Human FW3[b] | IGHV1-46 (70%) | IGlV7-46 (73%) |
| Closest Human J[b] | IGHJ6 (92%) | IGLJ1 (90%) |

Figure 3:
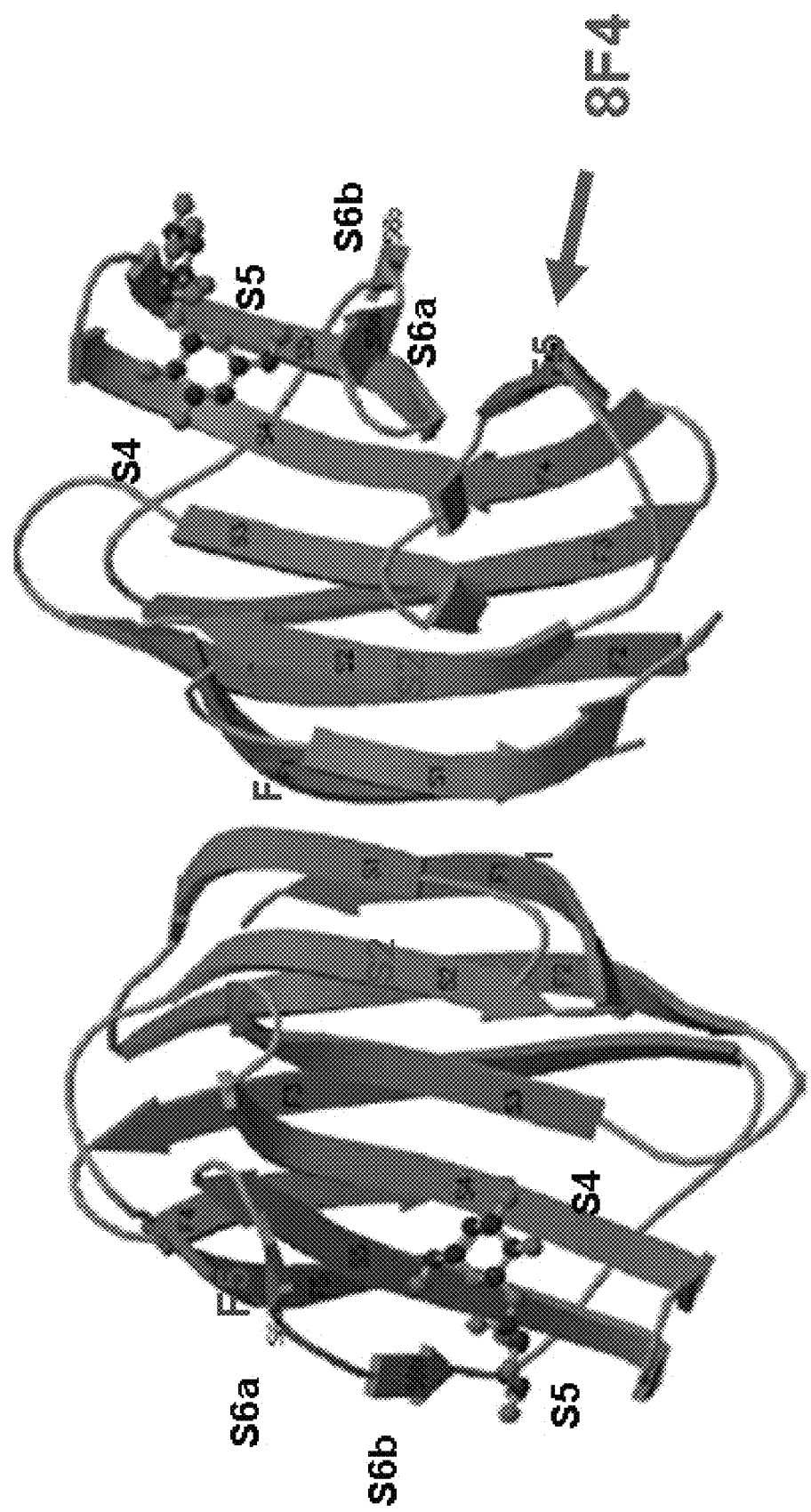
FIG. 3 shows a ribbon diagram of the homodimeric hGal1 with two lactose molecules prepared with MOLSCRIPT. The β-strands in the five-stranded (F1-F5) and six-stranded (S1-S6a/S6b) β-sheets are indicated by the letter-number code. The figure was adapted from Lopez-Lucendo et al. (2004) *J. Mol. Biol.* 343:957-970.
Figure 4:
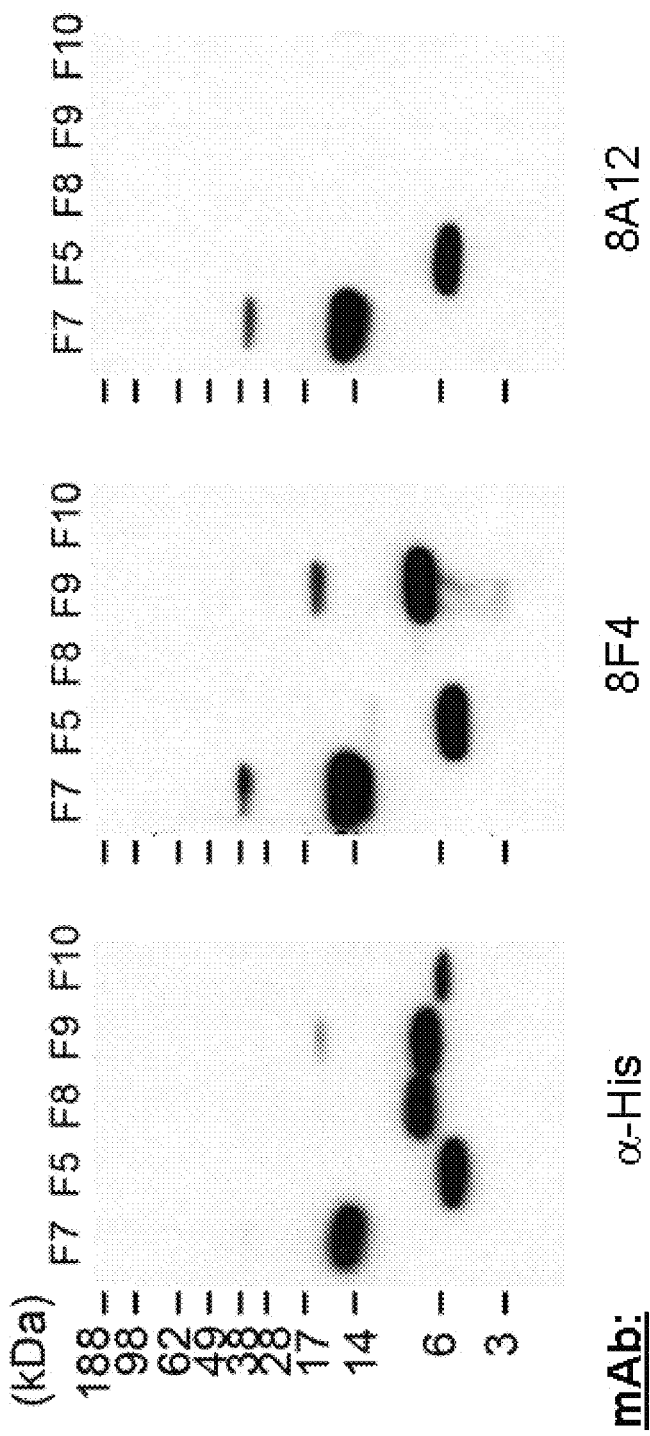
FIG. 4 shows the results of fine epitope mapping for the 8F4 mAb.
Figure 5:
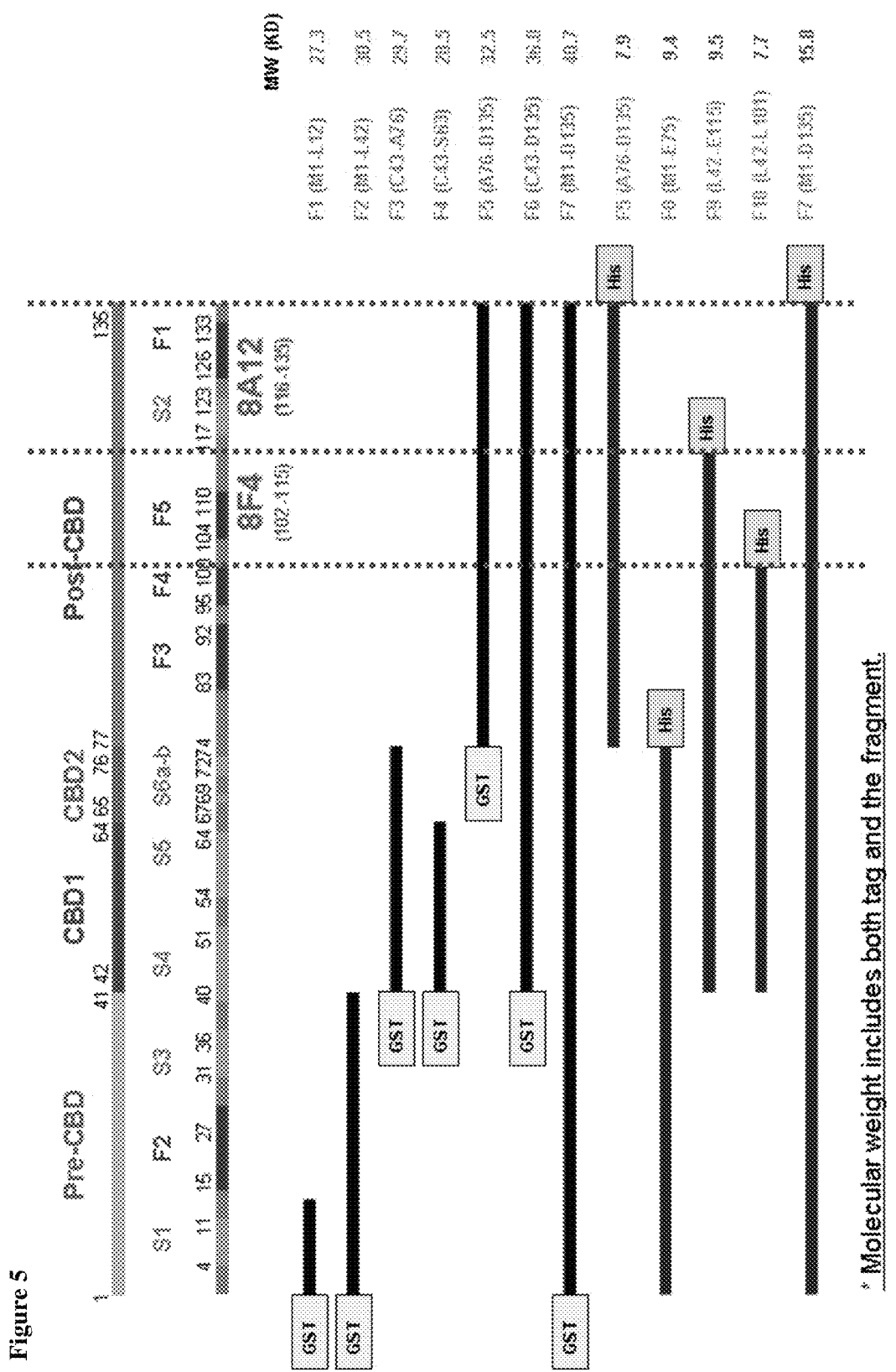
FIG. 5 shows a schematic diagram summarizing the fine epitope mapping results for the 8F4 mAb.

[a]CDR definitions and sequence numbering according to Kabat
[b]Germline ID(s) indicated followed by % homology Example 2: Fine Epitope Mapping of Neutralizing Anti-Gal1 Monoclonal Antibodies Useful for Therapeutic Applications The 8F4 mAb was determined to cross-react well with both human Gal1 and mouse Gal1 in FIG. 1 and recognize a post-CBD domain of Gal1 in Table 2 were further subjected to fine epitope mapping analyses. In addition to the seven GST-tagged human Gal1 constructs shown in FIG. 2 and produced in E. coli, five additional 6×HIS-tagged human Gal1 constructs spanning various portions of the human Gal1 polypeptide were generated in E. coli for use in epitope mapping analyses (FIG. 2). FIG. 2 further demonstrates how the amino acids encompassed by each GST-tagged and HIS-tagged construct maps with respect to the β-strands in the five-stranded β-sheets (F1-F5) and six-stranded β-sheets (S1-S6a/S6b) of the folded human Gal-1 polypeptide (FIG. 3). The Gal1-neutralizing 8F4 mAb was determined to recognize recombinant HIS-F7, HIS-F5, and HIS-F9 by Western blot analysis, whereas an anti-Gal1, non-neutralizing 8A12 mAb was determined to recognize recombinant HIS-F7 and HIS-F5 by Western blot analysis (FIG. 3). These results indicate that the 8F4 mAb binds Gal1 within amino acid residues 102-115, whereas the 8A12 mAb binds Gal1 within amino acid residues 116-135 (FIG. 5). In addition, such fine epitope mapping data define a structural basis for Gal1 neutralization because the human Gal1- neutralizing 8F4 mAb recognize the β-sheet F5 to thereby sterically interfere with and hinder the binding of human Gal1 to glycans (FIG. 3). By contrast, the non-neutralizing 8A12 mAb binds to β-sheets S2/F1, which is spatially far away from the carbohydrate binding domain.

Figure 6:
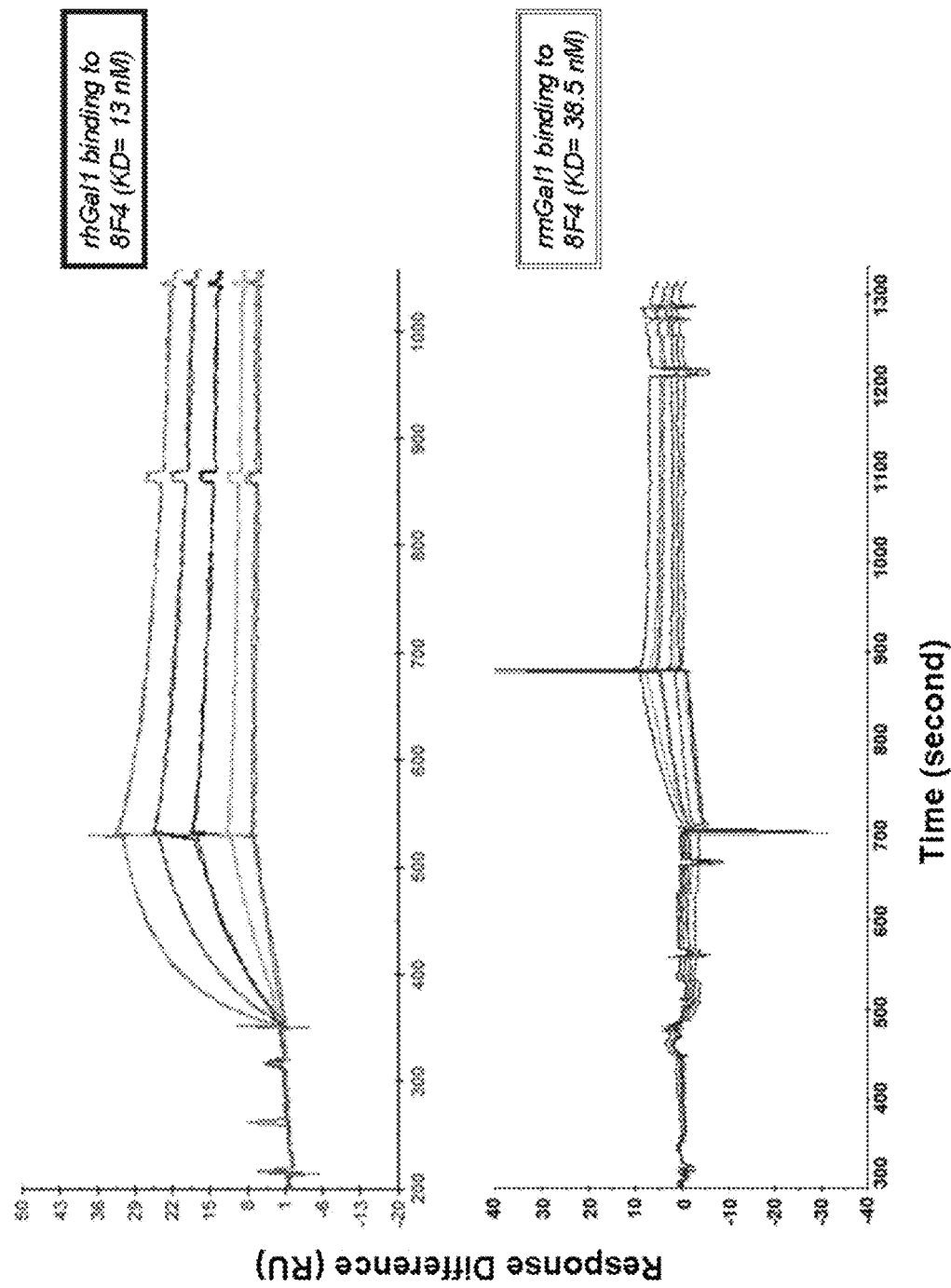
FIG. 6 shows the results of BlAcore analyses for the 8F4 mAb.
Figure 7:
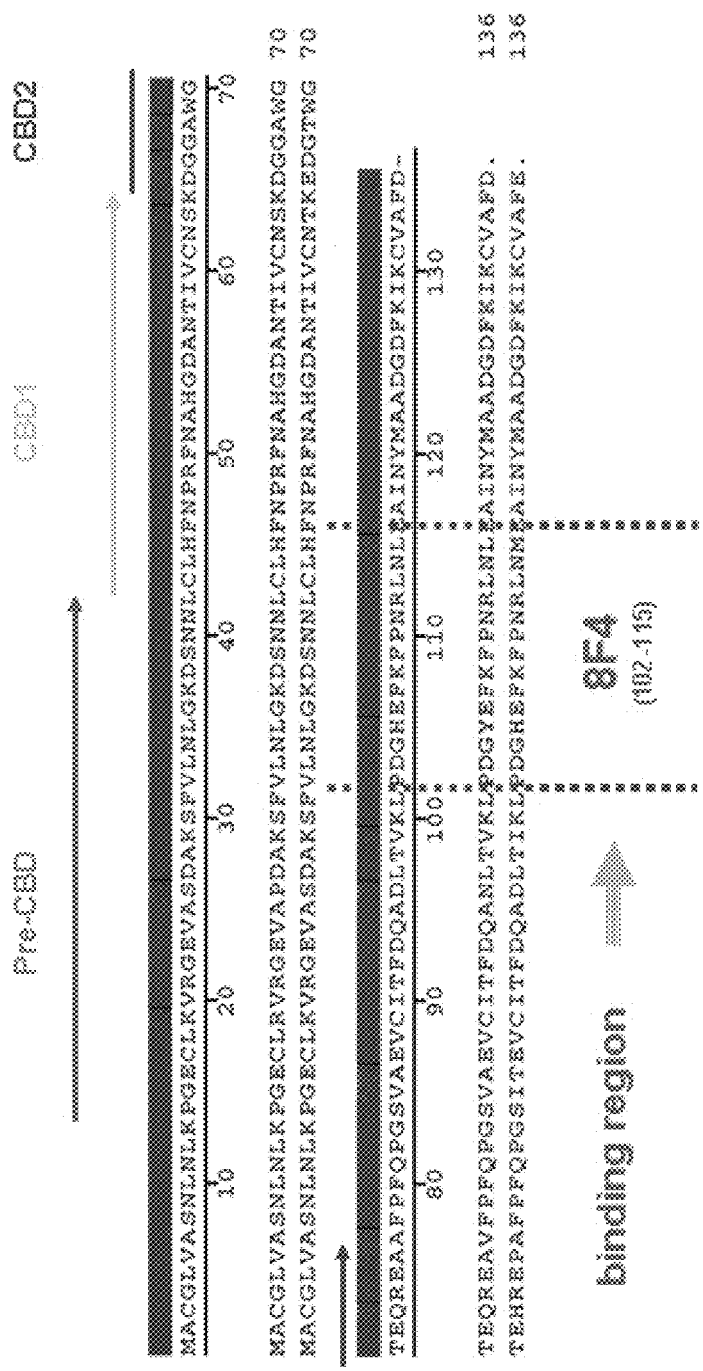
FIG. 7 shows a sequence comparison between mouse Gal1 (mGal1) and hGal1 in the region surrounding and including the epitope that 8F4 mAb binds.

Example 3: Biophysical Properties of Neutralizing Anti-Gal1 Monoclonal Antibodies Useful for Therapeutic Applications Surface Plasmon Resonance (SPR) analyses (also called Biomolecular Interaction Analysis, BIAcore) were also conducted in order to further define the biophysical properties (e.g., $k_{on}$, $k_{off}$, $k_{off}k_{on}$ ($K_D$) of Gal1's interaction with the 8F4 mAb. SPR experiments were performed at 25° C. in the standard BIAcore running buffer HBS-EP on a BIAcore 3000 Instrument (BIAcore). In brief, anti-mouse antibody was first captured on the CM-5 sensor chip (GE Health-Care). Afterwards, approximately 250 response units (RU) of the 8F4 anti-Gal1 mAb were immobilized (with exception of ~350 RU for rmGal1 assay) and followed by various dilutions of recombinant galectin (human galetin-1, 2, 3, 4, 7, 8, 9 or murine galectin-1 (mGal1), from R&D Systems) to assess the binding of galectin to 8F4. All data are shown after subtraction from a channel loaded with buffer alone. Data analysis to obtain the binding curves shown and equilibrium dissociation constant (KD) was performed using BIAevaluation 3.1 (BIAcore) by globally fitting the data to a simple 1:1 (Langmuir) binding model. The 8F4 mAb showed nanomolar (nM) levels of affinity with both recombinant hGal1 and recombinant mGal1, but with higher affinity for rhGal1 (KD of 13 nM for rhGal1 compared to 38.5 nM for rmGal1 (FIG. 6). In addition, the 8F4 mAb showed no binding or non-specific binding to higher concentrations of other recombinant galectins, including Gal2, Gal3, Gal4, Gal7, Gal8, and Gal9.

Example 4: Selectivity of Neutralizing Anti-Gal1 Monoclonal Antibodies Useful for Therapeutic Applications The significant preference for binding of rhGal1 by the 8F4 mAb over binding rmGal1 provides additional explanation for the observation that the 8F4 mAb is relatively less effective in blocking mGal1 in in vivo murine tumor models. In addition, six of the twenty (35%) amino acids in the region C61-F80 in the CBD adjacent to the epitope that 8F4 mAb binds are different between mGal1 and hGal1. These amino acid differences are believed to alter the conformation of the CBD and limit the efficiency of 8F4-mediated blockade of mGal1. This effect is further believed to be compounded by the fact that there are two amino acid differences in the murine and human epitopes that 8F4 mAb binds. Thus, the use of pre-clinical murine tumor models for assessing the suitability of the 8F4 mAb for clinical development in humans should be balanced by the fact that the 8F4 mAb has a higher affinity for hGal1 than for mGal1.

Such use is contemplated with or without combination with additional agents, such as inhibitors of immune checkpoing inhibitors. For example, programmed cell death ligand 1 (PD-L1, also known as B7-H1/CD274) is a cell-surface glycoprotein belonging to the B7 family of costimulatory molecules primarily expressed by antigen-presenting cells and that serve to regulate the cellular immune response (Zou et al. (2008) Nat. Rev. Immunol. 8:467-477; Keir et al. (2008) Annu. Rev. Immunol. 26:677-704). Binding of PD-L1 to its cognate receptor PD-1 inhibits proliferation of activated T cells in peripheral tissues leading to "T-cell exhaustion," a functional phenotype that can be reversed by PD-1 blockade (Barber et al. (2006) Nature 439:682-687; Freeman et al. (2000) J Exp Med. 192:1027-1034; Dong et al. (1999) Nat. Med. 5:1365-1369). Many human malignancies, including carcinomas of lung, ovary, and colon; melanomas; anaplastic large cell lymphomas; adult T-cell lymphomas; and cutaneous T-cell lymphomas express PD-L1 whereas normal human tissues, except for monocytes, macrophages, and placental synctiotrophoblasts, do not express detectable levels of PD-L1 by immunohistochemistry (Keir et al. (2008) Annu. Rev. Immunol. 26:677-704; Dong et al. (2002) Nat. Med. 8:793-800; Konishi et al. (2004) Clin. Cancer Res. 10:5094-5100; Kozako et al. (2009) Leukemia 23:375-382; Andorsky et al. (2011) Clin. Cancer Res. 17:4232-4244; Kantekure et al. (2012) Am. J. Dermatopathol. 34:126-128; Wilcox et al. (2009) Blood 114:2149-2158; Wilcox et al. (2012) Eur. J. Haematol. 88:465-475). In vitro and preclinical studies have shown that disruption of the PD-1/PD-L1 interaction potentiates the immune response and promotes antitumor activity (Iwai et al. (2002) Proc. Natl. Acad. Sci. USA. 99:12293-12297). Recent Phase I clinical trials with humanized anti-PD-1 and anti-PD-L1 antibodies have produced durable clinical responses in a subset of patients with solid organ malignancies, most notably melanoma, non-small cell lung carcinoma, and renal-cell carcinoma, suggesting a promising line of therapy based on targeting the PD-1/PD-L1 axis (Brahmer et al. (2010) J. Clin. Oncol. 28:3167-3175; Brahmer et al. (2012) N. Engl. J. Med. 366:2455-2465; Topalian et al. (2012) N. Engl. J. Med. 366:2443-2454).

As described herein, Gal1 is another immunoregulatory molecule. It has been shown that Gal1 is expressed by a variety of solid tumors and lymphoproliferative disorders, including gastrointestinal malignancies, thyroid papillary carcinoma, laryngeal squamous cell carcinoma, cutaneous T-cell lymphoma, MLL-rearranged B-lymphoblastic lymphoma, and the Reed-Sternberg cells of classical Hodgkin lymphoma (cHL) (Cedeno-Laurent et al. (2012) Blood 119: 3534-3538; Juszczynski et al. (2010) Clin. Cancer. Res. 16:2122-2130; Saussez et al. (2007) International Journal of Oncology. 30:1109; Danguy et al. (2002) Biochim. Biophys. Acta. 1572:28528-28529; Yamamoto et al. (2008) Blood 111:3220-3224; Gandhi et al. (2007) Blood 110:1326-1329; Juszczynski et al. (2007) Proc. Natl. Acad. Sci. USA. 104: 13134-13139; Green et al. (2010) Blood 116:3268-3277; Green et al. (2012) Clin. Cancer Res. 18:1611-1618; Ouyang et al. (2011) Blood 117:4315-4322; Rodig et al. (2008) Clin. Cancer Res.14:3338-3344). Gal1 knockdown or blockade with functionally antagonistic antibodies results in tumor rejection in a T-cell dependent manner in pre-clinical models of melanoma and Kaposi sarcoma (KS) (Rabinovich (2005) Br. J. Cancer. 92:1188-1192; Rubinstein et al. (2004) Cancer Cell 5:241-251; Croci et al. (2012) J. Exp. Med. 209:1985-2000) and prevents Gal1-mediated apoptosis of CD8+ T cells targeting EBV infected human B-cells in a model of PTLD (Ouyang et al. (2011) Blood 117:4315-4322).

Multimodal and combinatorial approaches to cancer therapy are increasingly targeting multiple mechanisms involved in tumor pathogenesis Immune evasion is an emerging hallmark of cancer that presents an attractive target with several recent advances, including clinical trials with humanized antibodies directed against immune checkpoint molecules, such as CTLA4 and PD-1 (Hanahan et al. (2011) Cell 144:646-674 and Pardoll (2012) Nat. Rev. Cancer 12:252-264). Recent Phase I clinical trials with anti- PD-1 and anti-PD-L1 antibodies in patients with solid tumors demonstrate the need for a reliable method of identifying those tumors that express high levels of PD-L1 in order to improve treatment efficacy (Brahmer et al. (2010) *J. Clin. Oncol.* 28:3167-3175; Brahmer et al. (2012) *N. Engl. J. Med.* 366:2455-2465; and Topalian et al. (2012) *N. Engl. J. Med.* 366:2443-2454). In the trial with anti-PD-1, 9 of 25 cases that expressed any detectable tumor-associated PD-L1 by immunohistochemistry showed a durable clinical response, whereas no clinical effect was observed in those patients with tumors lacking detectable PD-L1 (Topalian et al. (2012) *N. Engl. J. Med.* 366:2443-2454). The data described herein demonstrates robust membranous PD-L1 staining in the majority of EBV-positive DLBCL of the elderly and immunocompromised, NPC, and ENKTCL cases. A minority of EBV-negative PTLD, EBV-negative DLBCL, PBL, and PEL cases were positive for PD-L1.

Gal1 is also an emerging immunomodulatory molecule that leads to apoptosis of T cells and blockade of Gal1 gene expression promotes tumor rejection in mouse models (Liu et al. (2005) *Nat. Rev. Cancer* 5:29-41 and Rubinstein et al. (2004) *Cancer Cell* 5:241-251). Gal1 staining has been determined to be found in the majority of EBV-positive DLBCL, ENKTCL, and PBL, as well as the HHV8-associated tumors KS and PEL. These data indicate that classes of virally-driven malignancies can benefit from targeted therapy against PD-L1 and Gal1 and provide a reliable method for identifying those cases that may specifically respond to such treatment.

In line with previous studies examining the AP-1 and EBV-dependent expression of PD-L1 and Gal1 in EBV-positive PTLD and cHL (Juszczynski et al. (2007) *Proc. Natl. Acad. Sci. USA.* 104:13134-13139, Green et al. (2012) *Clin. Cancer Res.* 18:1611-1618, Ouyang et al. (2011) *Blood* 117:4315-4322, Rodig et al. (2008) *Clin. Cancer Res.*14: 3338-3344), Gal1 and PD-L1 expression correlated with expression of p-cJun and JunB in EBV-positive DLBCL and ENKTCL. Most EBV-negative PTLD cases showed expression of JunB and p-cJun, despite being negative for EBV by previous EBER analysis, and a subset of these cases showed membranous PD-L1 staining. Some of these cases also showed cytoplasmic PD-L1 staining, which is of uncertain significance as it is likely that only membrane expression of PD-L1 would contribute to tumor immune evasion. These tumors were also uniformly negative for Gal1, in contrast to EBV-positive PTLD (Ouyang et al. (2011) *Blood* 117:4315-4322). Similarly, the majority of NPC cases had activated AP-1 signaling and strong PD-L1 staining but were negative for Gal1. For PBL and PEL, expression of the AP-1 components correlated well with Gal1 expression, but several cases were negative for PD-L1. Together, these data indicate alternative mechanisms for the upregulation of PD-L1 and Gal1 and that AP-1 activation or EBV-positivity is not sufficient for driving expression of Gal1.

Amplification of the 9p24 locus, as shown for cHL (Green et al. (2010) *Blood* 116:3268-3277), may be a common finding in tumors that overexpress PD-L1 but are negative for EBV or activated AP-1 components. Conversely, interrogation of tumors that harbor 9p24 amplification, such as gray zone lymphoma and breast carcinoma (Eberle et al. (2011) *Modern Pathology* 24:1586-1597 and Wu et al. (2012) *Oncogene* 31:333-341), for PD-L1 expression would further identify candidates for anti-PD-L1 immunotherapy. Alternatively, aberrant signaling through the STATS pathway, first demonstrated in ALK-positive T-cell lymphoma as a result of the NPM/ALK fusion protein (Marzec et al. (2008) *Proc. Natl. Acad. Sci. USA.* 105:20852-20857) can provide another mechanism for PD-L1 expression.

An interesting exception to the other EBV-positive malignancies is the absence of Gal1, PD-L1, and JunB/cJun staining in virtually all EBV-positive BL cases. It is known that the EBV latency program in BL is different from DLBCL (Vereide et al. (2011) *Blood* 117:1977-1985 and Bornkamm (2009) *Semin. Cancer Biol.* 19:351-365). Specifically, a smaller set of viral proteins are expressed in BL and LMP1 is not expressed. In studies of EBV-dependent expression of Gal1 and PD-L1 in PTLD and cHL, it was shown that Gal1 and PD-L1 expression was dependent specifically on LMP1 (Green et al. (2012) *Clin. Cancer Res.* 18:1611-1618 and Ouyang et al. (2011) *Blood* 117:4315-4322). Thus, lack of LMP1 in BL tumor cells may result in the failure to activate AP-1 signaling and consequently an absence of detectable Gal1 and PD-L1 expression. Furthermore, it has been shown that the Myc protein counteracts the expression of PD-L1 (Durand-Panteix et al. (2012) *J. Immunol.* 189:181-190). Thus, it is believed that BL tumor cells, by virtue of myc translocation/amplification and an altered EBV latency program, would not benefit from targeted therapy against Gal1 or PD-L1. This finding also raises the possibility of downregulation of PD-L1 in other tumors that overexpress Myc, such as so-called double hit DLBCL (Aukema et al. (2011) Blood 117:2319-2331).

For HHV8-postive malignancies KS and PEL, the majority of cases were positive for Gal1 and AP-1 components, but only one case of PEL showed membranous PD-L1 staining and only one case of KS showed cytoplasmic PD-L1 staining. Endothelial cells also stain for Gal1 requiring careful interpretation of KS, which represents a proliferation of endothelial-derived tumor cells. A recent analysis of Gal1 expression in KS included analysis of benign vascular proliferations and Gal1 was only upregulated in KS samples (Croci et al. (2012) *J. Exp. Med.* 209:1985-2000). Furthermore, the same neutralizing anti-Gal1 antibody used in previous studies was shown to attenuate abnormal angiogenesis and promote tumor regression in mouse models of KS (Croci et al. (2012) *J. Exp. Med.* 209:1985-2000).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm nih gov.

Equivalents

Those skilled in the art will recognize, or be able to ascertain using no more than routine experimentation, many equivalents to the specific embodiments of the present invention described herein. Such equivalents are intended to be encompassed by the following claims.

What is claimed is:

1. An immunogenic composition comprising (i) one or more peptides, wherein the peptides are selected from the group consisting of PDGYEFKFPNRLNL (residues 102-115 of SEQ ID NO: 2), PDGHEFKFPNRLNM (residues 102-115 of SEQ ID NO: 4), PDGYTFKFPNRLNL (residues 102-115 of SEQ ID NO: 12), and PEVEFEFPNRLGME (residues 102-115 of SEQ ID NO: 14) and (ii) an immune-effective amount of an adjuvant.

2. The immunogenic composition of claim 1, wherein said one or more peptides is covalently linked to a detectable label.

3. The immunogenic composition of claim 1, further comprising at least one additional immunostimulatory agent.

4. The immunogenic composition of claim 3, wherein the immunostimulatory agent is
   i) an adjuvant, and/or
   ii) an immune checkpoint inhibitor selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof.

5. The immunogenic composition of claim 1, wherein the composition is capable of eliciting neutralizing anti-Gal1 antibodies in a mammal.

6. The immunogenic composition of claim 5, wherein the mammal is a human.

7. A method of identifying a neutralizing anti-Gal1 antibody comprising
   (a) administering an effective amount of
      the one or more peptides of claim 1(i)
      and a pharmaceutically acceptable carrier to a subject, or to B cells in an in vitro cell culture system, to generate antibodies that neutralize Gal1; and
   (b) isolating anti-Gal1 antibodies
      that specifically bind to Gal1.

8. A method of making an isolated hybridoma which produces a neutralizing anti-Gal1 antibody that specifically binds to Gal1, comprising:
   a) immunizing a mammal with or contacting B cells with an effective amount of
      the one or more peptides of claim 1(i)
      and a pharmaceutically acceptable carrier;
   b) isolating splenocytes from the immunized mammal;
   c) fusing splenocytes from the immunized mammal or B cells with an immortalized cell line to form hybridomas; and
   d) screening individual hybridomas for production of an anti-Gal1 antibody which specifically binds to Gal1.

9. A method of eliciting an anti-Gal1 immune response in a subject comprising administering to the subject a therapeutically effective amount of
   the immunogenic composition of claim 1.

10. A method of inhibiting Gal1 activity in a subject comprising administering to the subject a therapeutically effective amount of
    the immunogenic composition of claim 1.

11. A method for delaying the onset of, or slowing the rate of progression of, a disease in a subject mediated by Gal1 activity, comprising administering to the subject a therapeutically effective amount of
    the immunogenic composition of claim 1.

12. The method of claim 9, further comprising administering at least one additional agent that upregulates an immune response, optionally wherein
    the at least one additional agent comprises an inhibitor of an immune checkpoint
    selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof.

13. The method of claim 10, further comprising administering at least one additional agent that upregulates an immune response, optionally wherein
    the at least one additional agent comprises an inhibitor of an immune checkpoint
    selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof.

14. The method of claim 11, further comprising administering at least one additional agent that upregulates an immune response, optionally wherein
    the at least one additional agent comprises an inhibitor of an immune checkpoint
    selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof.

15. The method of claim 11, wherein the Gal1-mediated disease is a Gal1-positive cancer, Gal1-mediated angiogenesis disorder, API-dependent lymphoid malignancies, MLL-rearranged ALL, EBV+ post-transplant lymphoproliferative disorder (PTDL), nasopharyngeal carcinoma, Kaposi's sarcoma, breast cancer, prostate cancer, lung cancer, pancreatic cancer, squamous cell carcinoma of the head and neck, hepatocellular carcinoma, or melanoma.

16. The method of claim 9, wherein
(i) the immunogenic composition is administered in a single dose, is administered in multiple doses, or is administered as part of a heterologous prime-boost regimen, and/or
(ii) the subject is a mammal, optionally wherein the mammal is a human.

17. The method of claim 10, where in the subject is a mammal, optionally wherein the mammal is a human.

18. The method of claim 11, where in the subject is a mammal, optionally wherein the mammal is a human.

* * * * *

SEQUENCE LISTING

<160> NUMBER OF SEQ ID NOS: 20

<210> SEQ ID NO 1
<211> LENGTH: 408
<212> TYPE: DNA
<213> ORGANISM: Homo sapiens

<400> SEQUENCE: 1

```
atggcttgtg gtctggtcgc cagcaacctg aatctcaaac ctggagagtg ccttcgagtg      60
cgaggcgagg tggctcctga cgctaagagc ttcgtgctga acctgggcaa agacagcaac     120
aacctgtgcc tgcacttcaa ccctcgcttc aacgccacg gcgacgccaa caccatcgtg      180
tgcaacagca aggacggcgg ggcctggggg accgagcagc gggaggctgt ctttcccttc     240
cagcctggaa gtgttgcaga ggtgtgcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct ttgactga                  408
```

<210> SEQ ID NO 2
<211> LENGTH: 135
<212> TYPE: PRT
<213> ORGANISM: Homo sapiens

<400> SEQUENCE: 2

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135
```

<210> SEQ ID NO 3
<211> LENGTH: 408
<212> TYPE: DNA
<213> ORGANISM: Mus musculus

<400> SEQUENCE: 3

```
atggcctgtg gtctggtcgc cagcaacctg aatctcaaac tggggaatg tctcaaagtt       60
cggggagagg tggcctcgga cgccaagagc tttgtgctga acctgggaaa agacagcaac     120
aacctgtgcc tacacttcaa tcctcgcttc aatgccatg gagacgccaa caccattgtg      180
tgtaacacca aggaagatgg gacctgggga accgaacacc gggaacctgc cttcccttc      240
cagcccggga gcatcacaga ggtgtgcatc acctttgacc aggctgacct gaccatcaag     300
ctgccagacg gacatgaatt caagttcccc aaccgcctca acatggaggc catcaactac     360
```
atggcggcgg atggagactt caagattaag tgcgtggcct ttgagtga      408

<210> SEQ ID NO 4
<211> LENGTH: 135
<212> TYPE: PRT
<213> ORGANISM: Mus musculus

<400> SEQUENCE: 4

Met Ala Cys Gly Leu Val Ala Ser Asn Leu Asn Leu Lys Pro Gly Glu
1               5                   10                  15

Cys Leu Lys Val Arg Gly Glu Val Ala Ser Asp Ala Lys Ser Phe Val
            20                  25                  30

Leu Asn Leu Gly Lys Asp Ser Asn Leu Cys Leu His Phe Asn Pro
        35                  40                  45

Arg Phe Asn Ala His Gly Asp Ala Asn Thr Ile Val Cys Asn Thr Lys
    50                  55                  60

Glu Asp Gly Thr Trp Gly Thr Glu His Arg Glu Pro Ala Phe Pro Phe
65                  70                  75                  80

Gln Pro Gly Ser Ile Thr Glu Val Cys Ile Thr Phe Asp Gln Ala Asp
                85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
        115                 120                 125

Ile Lys Cys Val Ala Phe Glu
    130                 135

<210> SEQ ID NO 5
<211> LENGTH: 408
<212> TYPE: DNA
<213> ORGANISM: Macaca mulatta

<400> SEQUENCE: 5
atggcttgtg gtctggtcgc cagcaacctg aatctcaaac ctggagagtg cctccgagtg      60
cggggcgagg tggccccga cgccaagagc ttcgtgctga acctgggcaa agatagcaac     120
aacctgtgcc tgcacttcaa ccctcgcttc aacgcccacg gcgacgccaa caccatcgtg     180
tgcaacagca aggacggtgg ggcctggggg accgagcagc gggaggctgc ctttcctttc     240
cagcctggaa gtgtcgcaga ggtgtgcatc acctttgacc aggccgacct gaccatcaag     300
ctgccagatg gatacgaatt caagttcccc aaccgcctca acctggaggc catcaactac     360
atggcagctg acggtgactt caagatcaag tgtgtggcct ttgactga                  408

<210> SEQ ID NO 6
<211> LENGTH: 135
<212> TYPE: PRT
<213> ORGANISM: Macaca mulatta

<400> SEQUENCE: 6

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Ala Phe Pro Phe
65                  70                  75                  80

Gln Pro Gly Ser Val Ala Glu Val Cys Ile Thr Phe Asp Gln Ala Asp
                85                  90                  95

Leu Thr Ile Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 7
<211> LENGTH: 408
<212> TYPE: DNA
<213> ORGANISM: Pan troglodytes

<400> SEQUENCE: 7
atggcttgtg gtctggtcgc cagcaacctg aatctcaaac ctggagagtg ccttcgagtg        60
cgaggcgagg tggcccctga cgctaagagc ttcgtgctga acctgggcaa agacagcaac       120
aacctgtgcc tgcacttcaa ccctcgcttc aacgcccacg gcgacgccaa caccatcgtg       180
tgcaacagca aggacggcgg ggcctggggg accgagcagc gggaggctgt ctttcccttc       240
cagcctggaa gtgttgcaga ggtgtgcatc accttcgacc aggccaacct gaccgtcaag       300
ctgccagatg gatacgaatt caagttcccc aaccgcctca acctggaggc catcaactac       360
atggcagctg acggtgactt caagatcaag tgtgtggcct ttgactga                    408

<210> SEQ ID NO 8
<211> LENGTH: 135
<212> TYPE: PRT
<213> ORGANISM: Pan troglodytes

<400> SEQUENCE: 8

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 9
<211> LENGTH: 408
<212> TYPE: DNA
<213> ORGANISM: Rattus norvegicus

<400> SEQUENCE: 9

```
atggcctgtg gtctggtcgc cagcaacctg aatctcaaac ctggggaatg tctcaaagtt      60
cggggagagc tggccccgga cgccaagagc tttgtgttga acctggggaa agacagcaac     120
aacctgtgcc tacacttcaa ccccgcttc aacgcccacg gagatgccaa caccattgtg      180
tgtaacagca aggacgatgg gacctgggga acagaacaac gggagactgc cttccctttc     240
cagcctggga gcatcacgga ggtgtgcatc acctttgacc aggctgacct gaccatcaag     300
ctgccagacg gcatgaatt caaattcccc aaccgcctca acatggaggc catcaactac      360
atggcggcgg atggtgactt caagattaag tgtgtggcct ttgagtga                  408
```

```
<210> SEQ ID NO 10
<211> LENGTH: 135
<212> TYPE: PRT
<213> ORGANISM: Rattus norvegicus

<400> SEQUENCE: 10
```

```
Met Ala Cys Gly Leu Val Ala Ser Asn Leu Asn Leu Lys Pro Gly Glu
1               5                   10                  15

Cys Leu Lys Val Arg Gly Glu Leu Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Asp Gly Thr Trp Gly Thr Glu Gln Arg Glu Thr Ala Phe Pro Phe
65                  70                  75                  80

Gln Pro Gly Ser Ile Thr Glu Val Cys Ile Thr Phe Asp Gln Ala Asp
                85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
        115                 120                 125

Ile Lys Cys Val Ala Phe Glu
    130                 135
```

```
<210> SEQ ID NO 11
<211> LENGTH: 408
<212> TYPE: DNA
<213> ORGANISM: Canis familiaris

<400> SEQUENCE: 11
```

```
atggcttgtg gtctggtcgc cagcaatctg agtctcaaac ctgggcagtg cctcagagtg      60
caatgcgagg tggtccccga agccaagagc ttcgtgctga acctgggcaa agacggggac     120
aacctgtgcc tgcacttcaa ccctcgcttt gaagcccatg cgacgtcaa caccattgtg      180 tgtaacagca aggatggcgg ggcctggggc gaggagcttc gagagtccgc cttcccttc      240 cagcccggga ctgtcacaga ggtgtgcatc tccttcgacc aggctgactt gaccatcaag     300
ctgccagatg gatacaccct caagttcccc aaccgcctca acctggaggc catcagctac     360
ctggcagctg atggtgacat gaagatcaag tgcctggcct ttgactaa                  408
```

```
<210> SEQ ID NO 12
<211> LENGTH: 135
<212> TYPE: PRT
<213> ORGANISM: Canis familiaris

<400> SEQUENCE: 12
```

```
Met Ala Cys Gly Leu Val Ala Ser Asn Leu Ser Leu Lys Pro Gly Gln
1               5                   10                  15

Cys Leu Arg Val Gln Cys Glu Val Val Pro Glu Ala Lys Ser Phe Val
            20                  25                  30

Leu Asn Leu Gly Lys Asp Gly Asp Asn Leu Cys Leu His Phe Asn Pro
        35                  40                  45

Arg Phe Glu Ala His Gly Asp Val Asn Thr Ile Val Cys Asn Ser Lys
    50                  55                  60

Asp Gly Gly Ala Trp Gly Glu Leu Arg Glu Ser Ala Phe Pro Phe
65                  70                  75                  80

Gln Pro Gly Thr Val Thr Glu Val Cys Ile Ser Phe Asp Gln Ala Asp
                85                  90                  95

Leu Thr Ile Lys Leu Pro Asp Gly Tyr Thr Phe Lys Phe Pro Asn Arg
            100                 105                 110

Leu Asn Leu Glu Ala Ile Ser Tyr Leu Ala Ala Asp Gly Asp Met Lys
        115                 120                 125

Ile Lys Cys Leu Ala Phe Asp
        130                 135

<210> SEQ ID NO 13
<211> LENGTH: 405
<212> TYPE: DNA
<213> ORGANISM: Gallus gallus

<400> SEQUENCE: 13
atggagcaag gactggttgt tacccagctg gatgtacagc ctggagagtg tgtcaaggtc      60
aaagggaaga tcctatccga tgccaaaggg ttttctgtga atgtagggaa ggacagcagc     120
acactcatgc ttcatttcaa ccctcgcttt gactgccatg gggatgtcaa cactgttgtg     180
tgcaactcaa aggaggatgg cacgtggggt gaggaggaca ggaaggctga cttccctttc     240
cagcagggcg acaaggttga gatctgtatc tcctttgatg cagcagaggt caaggtgaag     300
gtgcctgaag tggagtttga gtttcccaat cggctgggca tggagaaaat tcaataccctg    360 gctgtggagg gtgactttaa agtgaaagct attaagttca gctaa                    405

<210> SEQ ID NO 14
<211> LENGTH: 134
<212> TYPE: PRT
<213> ORGANISM: Gallus gallus

<400> SEQUENCE: 14

Met Glu Gln Gly Leu Val Val Thr Gln Leu Asp Val Gln Pro Gly Glu
1               5                   10                  15

Cys Val Lys Val Lys Gly Lys Ile Leu Ser Asp Ala Lys Gly Phe Ser
            20                  25                  30

Val Asn Val Gly Lys Asp Ser Ser Thr Leu Met Leu His Phe Asn Pro
        35                  40                  45

Arg Phe Asp Cys His Gly Asp Val Asn Thr Val Val Cys Asn Ser Lys
    50                  55                  60

Glu Asp Gly Thr Trp Gly Glu Glu Asp Arg Lys Ala Asp Phe Pro Phe
65                  70                  75                  80

Gln Gln Gly Asp Lys Val Glu Ile Cys Ile Ser Phe Asp Ala Ala Glu
                85                  90                  95

Val Lys Val Lys Val Pro Glu Val Glu Phe Glu Phe Pro Asn Arg Leu
            100                 105                 110
```

```
Gly Met Glu Lys Ile Gln Tyr Leu Ala Val Glu Gly Asp Phe Lys Val
        115                 120                 125

Lys Ala Ile Lys Phe Ser
    130
```

<210> SEQ ID NO 15
<211> LENGTH: 408
<212> TYPE: DNA
<213> ORGANISM: Bos taurus

<400> SEQUENCE: 15

```
atggcttgtg gtctggtcgc cagcaacctg aatctcaaac ctggggagtg cctcagagtg    60
cggggcgagg tggccgcaga cgccaagagc ttcttgctga acctgggcaa agacgacaac   120
aacctgtgcc tccacttcaa ccctcgtttc aacgcgcatg gggacgtcaa caccatcgtg   180
tgtaacagca aggacgctgg ggcctggggg gccgagcaga gggaatctgc cttcccttc    240 cagcctggaa gtgtcgtgga ggtatgcatc tccttcaacc agacggacct aaccatcaag   300
ctgcctgatg gatacgaatt caagttcccc aaccgcctca acctggaggc catcaactac   360
ctgtctgcag gtggtgactt caagatcaag tgtgtggcct ttgagtga               408
```

<210> SEQ ID NO 16
<211> LENGTH: 135
<212> TYPE: PRT
<213> ORGANISM: Bos taurus

<400> SEQUENCE: 16

```
Met Ala Cys Gly Leu Val Ala Ser Asn Leu Asn Leu Lys Pro Gly Glu
1               5                   10                  15

Cys Leu Arg Val Arg Gly Glu Val Ala Ala Asp Ala Lys Ser Phe Leu
            20                  25                  30

Leu Asn Leu Gly Lys Asp Asp Asn Asn Leu Cys Leu His Phe Asn Pro
        35                  40                  45

Arg Phe Asn Ala His Gly Asp Val Asn Thr Ile Val Cys Asn Ser Lys
    50                  55                  60

Asp Ala Gly Ala Trp Gly Ala Glu Gln Arg Glu Ser Ala Phe Pro Phe
65                  70                  75                  80

Gln Pro Gly Ser Val Val Glu Val Cys Ile Ser Phe Asn Gln Thr Asp
                85                  90                  95

Leu Thr Ile Lys Leu Pro Asp Gly Tyr Glu Phe Lys Phe Pro Asn Arg
            100                 105                 110

Leu Asn Leu Glu Ala Ile Asn Tyr Leu Ser Ala Gly Gly Asp Phe Lys
        115                 120                 125

Ile Lys Cys Val Ala Phe Glu
    130                 135
```

<210> SEQ ID NO 17
<211> LENGTH: 354
<212> TYPE: DNA
<213> ORGANISM: Artificial Sequence
<220> FEATURE:
<223> OTHER INFORMATION: /note="Description of Artificial Sequence: 8B5, 8F4, and 8G3 vH cDNA sequence"

<400> SEQUENCE: 17

```
gaggttcagc tgcagcagtc tgtggcagag tttgtgaggc caggggcctc agtcaggttg    60
tcctgcacag cttctggctt caacattaaa aacacctata tacactgggt gaggcagagg   120
cctgaacagg gcctggagtg gattggaaag attgatcctg cgaatggtaa tactaaatat   180
```

```
gtcccggagt tccagggcaa ggccactatg actgcggaca catcctccaa cacagtctac    240
ctgcacctca gcagcctgac atctgaggac actgccatct attactgtgt cgatggttac    300
tacggctggt atttcgctgt ctggggcaca gggaccacgg tcaccgtctc ctca          354
```

```
<210> SEQ ID NO 18
<211> LENGTH: 327
<212> TYPE: DNA
<213> ORGANISM: Artificial Sequence
<220> FEATURE:
<223> OTHER INFORMATION: /note="Description of Artificial Sequence: 8B5,
      8F4, and 8G3 vK cDNA sequence"

<400> SEQUENCE: 18
```

```
caggctgttg tgactcagga atctgcactc accacatcac ctggtgaaac agtcacactc    60
acttgtcgct caagcactgg ggctgttaca actagtaact atgccaactg ggtccaagaa    120
aaaccagatc atttattcac tggtctaata ggtgctacca caaaccgagc tccaggtgtt    180
cctgccagat tctcaggctc cctgattgga gacaaggctg tcctcaccat cacagggca    240 caaactgagg atgaggcaat atatttctgt gctctatggt acagaaacca ttttattttc    300
ggcagtggaa ccaaggtcac tgtcctc                                        327
```

```
<210> SEQ ID NO 19
<211> LENGTH: 118
<212> TYPE: PRT
<213> ORGANISM: Artificial Sequence
<220> FEATURE:
<223> OTHER INFORMATION: /note="Description of Artificial Sequence: 8B5,
      8F4, and 8G3 vH amino acid sequence"

<400> SEQUENCE: 19
```

```
Glu Val Gln Leu Gln Gln Ser Val Ala Glu Phe Val Arg Pro Gly Ala
1               5                   10                  15

Ser Val Arg Leu Ser Cys Thr Ala Ser Gly Phe Asn Ile Lys Asn Thr
            20                  25                  30

Tyr Ile His Trp Val Arg Gln Arg Pro Glu Gln Gly Leu Glu Trp Ile
        35                  40                  45

Gly Lys Ile Asp Pro Ala Asn Gly Asn Thr Lys Tyr Val Pro Glu Phe
    50                  55                  60

Gln Gly Lys Ala Thr Met Thr Ala Asp Thr Ser Ser Asn Thr Val Tyr
65                  70                  75                  80

Leu His Leu Ser Ser Leu Thr Ser Glu Asp Thr Ala Ile Tyr Tyr Cys
                85                  90                  95

Val Asp Gly Tyr Tyr Gly Trp Tyr Phe Ala Val Trp Gly Thr Gly Thr
            100                 105                 110

Thr Val Thr Val Ser Ser
        115
```

```
<210> SEQ ID NO 20
<211> LENGTH: 109
<212> TYPE: PRT
<213> ORGANISM: Artificial Sequence
<220> FEATURE:
<223> OTHER INFORMATION: /note="Description of Artificial Sequence: 8B5,
      8F4, and 8G3 vK amino acid sequence"

<400> SEQUENCE: 20
```

```
Gln Ala Val Val Thr Gln Glu Ser Ala Leu Thr Thr Ser Pro Gly Glu
1               5                   10                  15
```

-continued

```
Thr Val Thr Leu Thr Cys Arg Ser Ser Thr Gly Ala Val Thr Thr Ser
            20              25              30

Asn Tyr Ala Asn Trp Val Gln Glu Lys Pro Asp His Leu Phe Thr Gly
        35              40              45

Leu Ile Gly Ala Thr Asn Asn Arg Ala Pro Gly Val Pro Ala Arg Phe
    50              55              60

Ser Gly Ser Leu Ile Gly Asp Lys Ala Val Leu Thr Ile Thr Gly Ala
65              70              75              80

Gln Thr Glu Asp Glu Ala Ile Tyr Phe Cys Ala Leu Trp Tyr Arg Asn
            85              90              95

His Phe Ile Phe Gly Ser Gly Thr Lys Val Thr Val Leu
            100             105
```